US008906027B2

(12) United States Patent
Roche

(10) Patent No.: US 8,906,027 B2
(45) Date of Patent: Dec. 9, 2014

(54) SYSTEM AND METHOD FOR ORTHOPEDIC DISTRACTION AND STABILIZATION

(76) Inventor: Martin Roche, Fort Lauderdale, FL (US)

( * ) Notice: Subject to any disclaimer, the term of this patent is extended or adjusted under 35 U.S.C. 154(b) by 363 days.

(21) Appl. No.: 12/748,147

(22) Filed: Mar. 26, 2010

(65) Prior Publication Data

US 2010/0249788 A1   Sep. 30, 2010

Related U.S. Application Data

(60) Provisional application No. 61/211,023, filed on Mar. 26, 2009, provisional application No. 61/221,761, filed on Jun. 30, 2009, provisional application No. 61/221,767, filed on Jun. 30, 2009, provisional application No. 61/221,779, filed on Jun. 30, 2009, provisional application No. 61/221,788, filed on Jun. 30, 2009, provisional application No. 61/221,793, filed on Jun. 30, 2009, provisional application No. 61/221,801, filed on Jun. 30, 2009, provisional application No. 61/221,808, filed on Jun. 30, 2009, provisional application No. 61/221,817, filed on Jun. 30, 2009, provisional application No. 61/221,867, filed on Jun. 30, 2009, provisional application No. 61/221,874, filed on Jun. 30, 2009, provisional application No. 61/221,879, filed on Jun. 30, 2009, provisional application No. 61/221,881, filed on Jun. 30, 2009, provisional application No. 61/221,886, filed on Jun. 30, 2009, provisional application No. 61/221,889, filed on Jun. 30, 2009, provisional application No. 61/221,894, filed on Jun. 30, 2009, provisional application No. 61/221,901, filed on Jun. 30, 2009, provisional application No. 61/221,909, filed on Jun. 30, 2009, provisional application No. 61/221,916, filed on Jun. 30, 2009, provisional application No. 61/221,923, filed on Jun. 30, 2009, provisional application No. 61/221,929, filed on Jun. 30, 2009.

(51) Int. Cl.
| | | |
|---|---|---|
| A61B 17/58 | (2006.01) | |
| A61B 17/60 | (2006.01) | |
| A61F 2/00 | (2006.01) | |
| A61B 5/00 | (2006.01) | |
| G06Q 50/22 | (2012.01) | |
| G06Q 50/24 | (2012.01) | |
| A61B 5/107 | (2006.01) | |
| A61B 17/02 | (2006.01) | |
| A61B 17/00 | (2006.01) | |
| A61B 19/00 | (2006.01) | |

(52) U.S. Cl.
CPC ....... *A61B 5/4528* (2013.01); *A61B 2017/0268* (2013.01); *A61B 5/412* (2013.01); *A61B 2017/00221* (2013.01); *G06Q 50/22* (2013.01); *G06Q 50/24* (2013.01); *A61B 5/4509* (2013.01); *A61B 2019/464* (2013.01); *A61B 17/025* (2013.01); *A61B 5/1076* (2013.01)
USPC ............... 606/90; 606/88; 606/86 R; 606/102

(58) Field of Classification Search
USPC ................. 606/86 R, 87–90, 102; 623/13.13, 623/20.32, 20.33, 20.15; 600/587, 588, 595
See application file for complete search history.

(56) References Cited

U.S. PATENT DOCUMENTS

| | | | |
|---|---|---|---|
| 5,470,354 A | 11/1995 | Hershberger et al. | |
| 5,569,260 A * | 10/1996 | Petersen | ......................... 606/88 |

(Continued)

*Primary Examiner* — Matthew Lawson
*Assistant Examiner* — Si Ming Lee

(57) ABSTRACT

At least one embodiment is directed to a dynamic distractor (1 00) for distracting bones of a muscular-skeletal system. The dynamic distractor (100) includes at least one sensor (108, 110) which can provide loading, loading differential and position information as well as other measured parameters, a handle (112, 804), a lift mechanism (302), and one or more alignment aid (502, 802). The position and measurement sensors (108, 110) communicate with the processing unit (406) to display, process, and store measured data. A rod (604) couples a cutting block (602) to the distractor (100). The rod (604) also fixes a position of a cutting block (602) in relation to the distractor (100). The cutting block (602) is coupled to the distractor (100) to stabilize and align the muscular-skeletal system while shaping a bone.

8 Claims, 19 Drawing Sheets

(56) References Cited

U.S. PATENT DOCUMENTS

| | | | |
|---|---|---|---|
| 5,669,914 A * | 9/1997 | Eckhoff | 606/88 |
| 5,683,396 A | 11/1997 | Tokish et al. | |
| 5,688,279 A | 11/1997 | McNulty et al. | |
| 5,871,018 A | 2/1999 | Delp et al. | |
| 6,245,109 B1 | 6/2001 | Mendes et al. | |
| 6,583,630 B2 | 6/2003 | Mendes et al. | |
| 6,621,278 B2 | 9/2003 | Ariav | |
| 6,701,174 B1 | 3/2004 | Krause et al. | |
| 6,856,141 B2 | 2/2005 | Ariav | |
| 7,195,645 B2 | 3/2007 | Disilvestro et al. | |
| 7,442,196 B2 | 10/2008 | Fisher et al. | |
| 7,578,821 B2 * | 8/2009 | Fisher et al. | 606/88 |
| 2002/0029784 A1 | 3/2002 | Stark et al. | |
| 2003/0069644 A1 * | 4/2003 | Kovacevic et al. | 623/20.32 |
| 2003/0187452 A1 * | 10/2003 | Smith et al. | 606/88 |
| 2005/0020941 A1 | 1/2005 | Tarabichi | |
| 2006/0058798 A1 | 3/2006 | Roman et al. | |
| 2006/0232408 A1 | 10/2006 | Nyez et al. | |
| 2006/0271112 A1 | 11/2006 | Martinson et al. | |
| 2007/0219561 A1 | 9/2007 | Lavalle et al. | |
| 2007/0272747 A1 | 11/2007 | Woods et al. | |
| 2007/0282451 A1 * | 12/2007 | Metzger et al. | 623/20.28 |
| 2009/0222089 A1 * | 9/2009 | Hauri et al. | 623/13.13 |
| 2009/0270869 A1 * | 10/2009 | Colquhoun et al. | 606/88 |
| 2010/0191068 A1 * | 7/2010 | Bewernitz et al. | 600/300 |

* cited by examiner

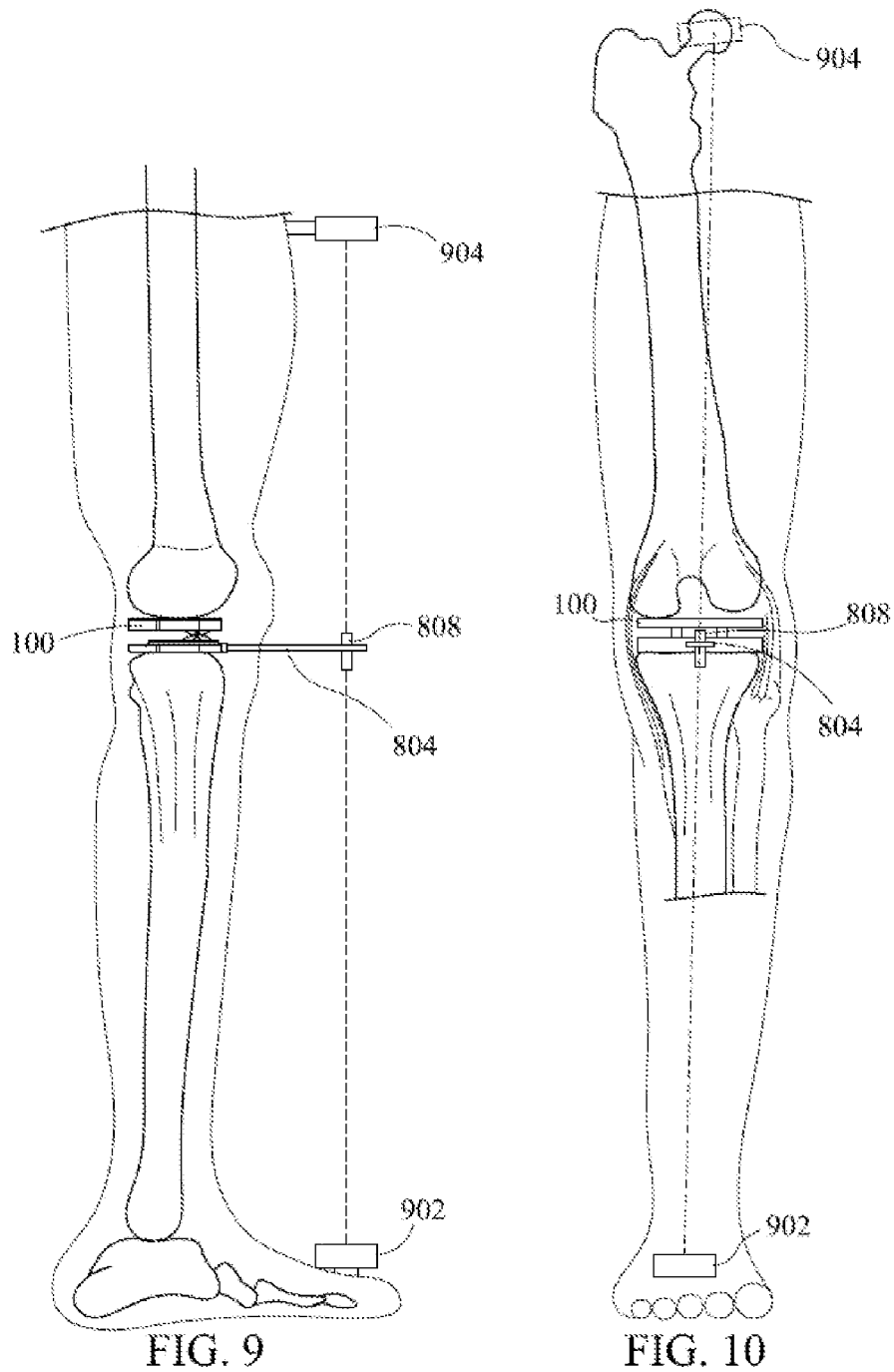

1700

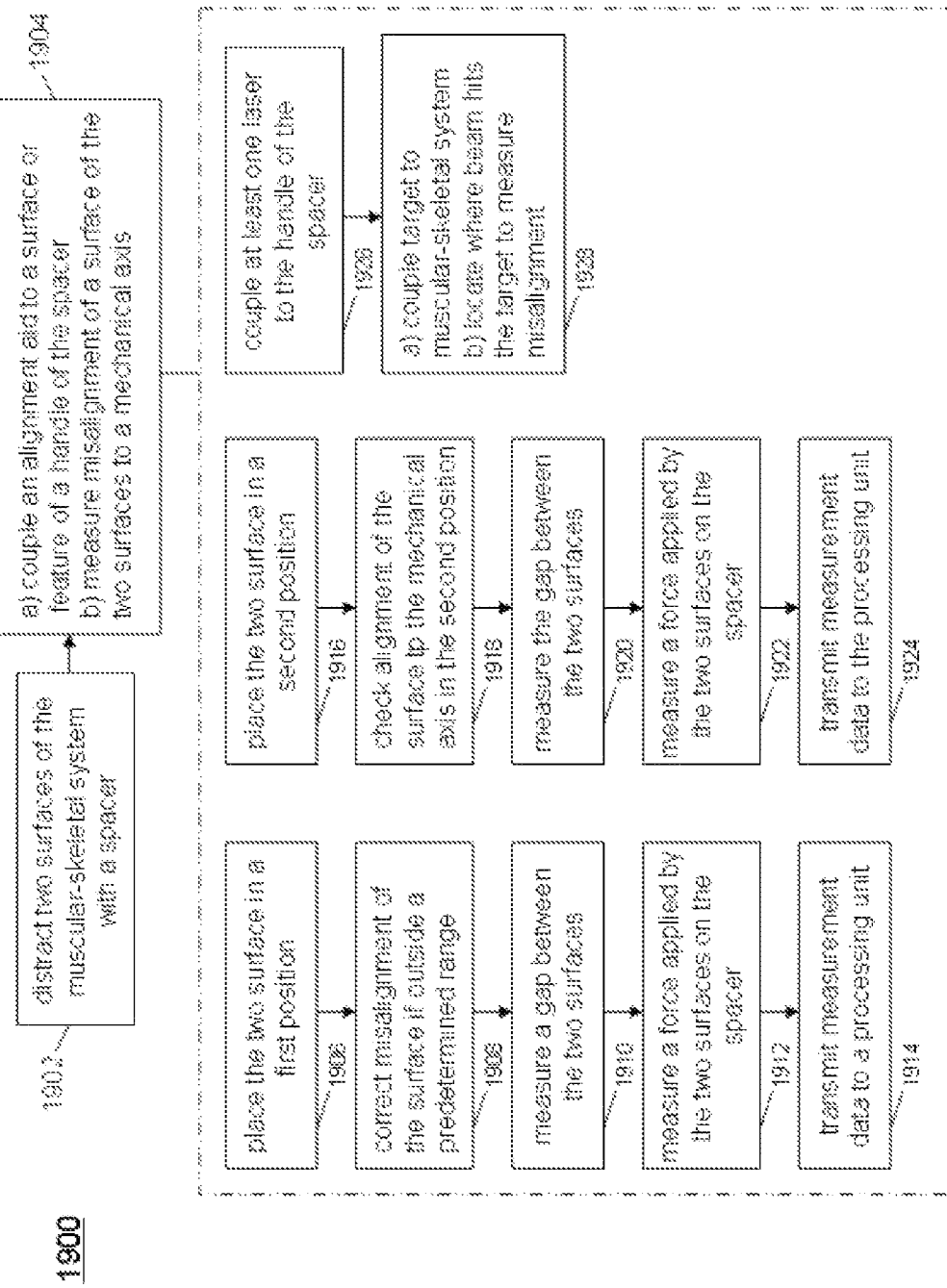

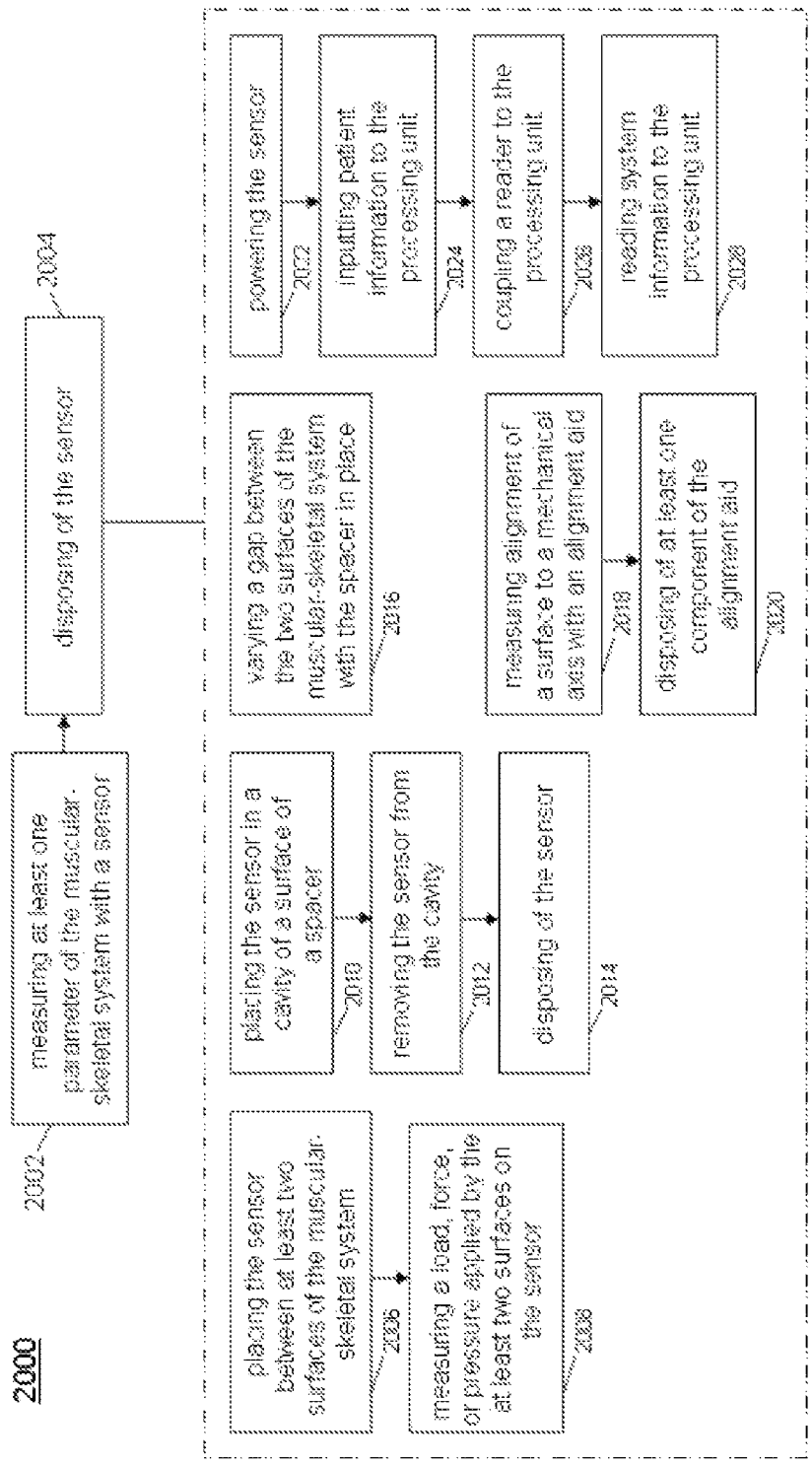

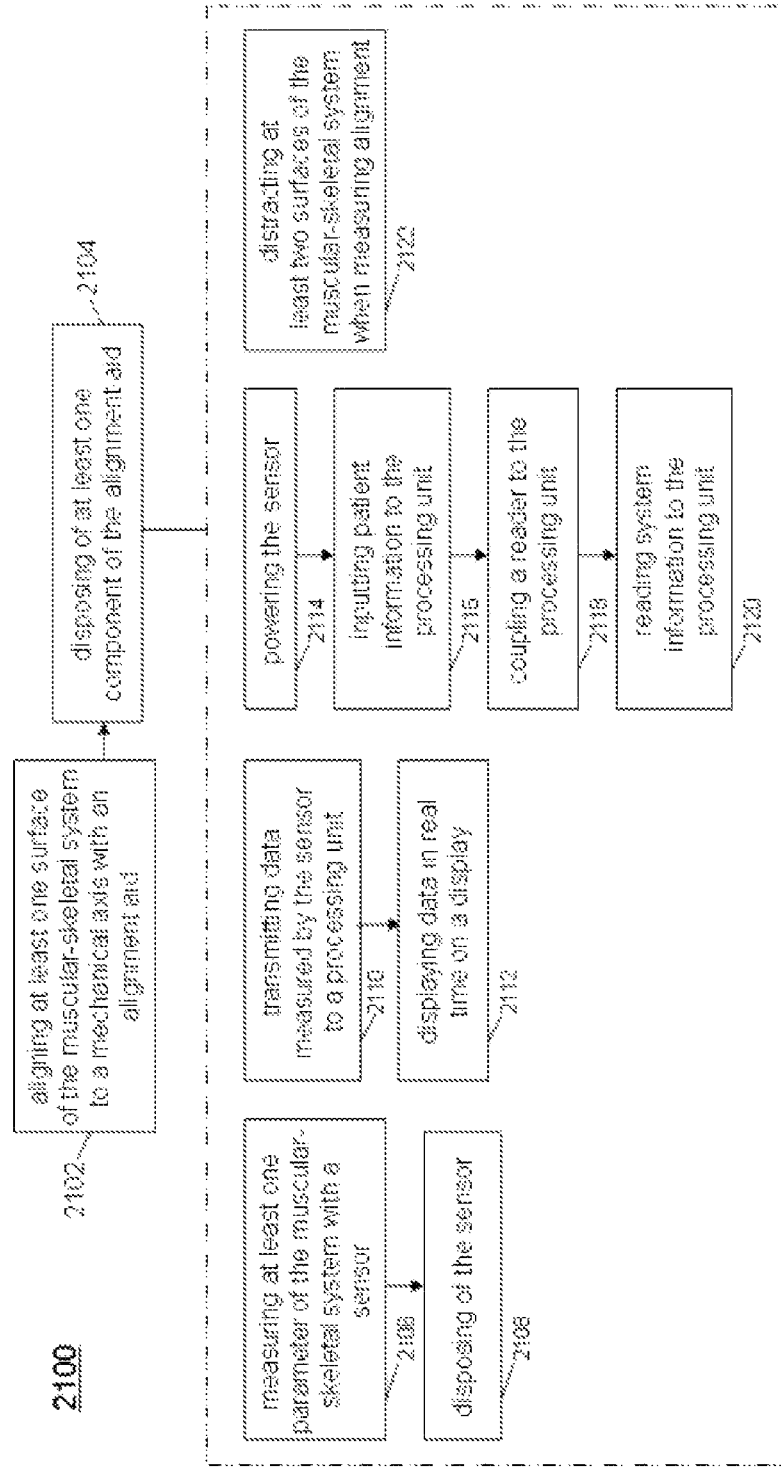

SYSTEM AND METHOD FOR ORTHOPEDIC DISTRACTION AND STABILIZATION

CROSS-REFERENCE

This application claims the priority benefits of U.S. Provisional Patent Application No. 61/211,023 filed on Mar. 26, 2009, the entire contents of which are hereby incorporated by reference. This application further claims the priority benefit of U.S. provisional patent applications No. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, 61/221,923, and 61/221,929 all filed 30 Jun. 2009. The disclosures of which are incorporated herein by reference in its entirety.

FIELD

The disclosure relates in general to orthopedics, and particularly though not exclusively, is related to a device and method to facilitate orthopedic surgery.

BACKGROUND

The skeletal system is a balanced support framework subject to variation and degradation. Changes in the skeletal system can occur due to environmental factors, degeneration, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction. The spinal column is comprised of vertebrae, discs, ligaments, and muscles that stabilize the vertebral column and protects the spinal nerves.

There has been substantial growth in the repairing of the human skeletal system as orthopedic joint implant technology has evolved. In general, improvements to orthopedic implant joints have been based on empirical data that is sporadically gathered from real patients. Similarly, the majority of implant surgeries are being performed with tools that have not changed substantially in decades but have been refined over time. In general, the orthopedic implant procedure has been standardized to meet the needs of the general population. Adjustments due to individual skeletal variations rely on the skill of the surgeon to adjust the process for the exact circumstance. At issue is that there is little or no data during an orthopedic surgery, post-operatively, and long term that provides feedback to the orthopedic manufacturers and surgeons about the implant status.

BRIEF DESCRIPTION OF THE DRAWINGS

Exemplary embodiments will become more fully understood from the detailed description and the accompanying drawings, wherein:

FIG. 9 is a side view of a leg in extension with a dynamic distractor in the knee joint region in accordance with an exemplary embodiment;

FIG. 10 is a top view of a leg in extension with a dynamic distractor in the knee joint area in accordance with an exemplary embodiment;

FIG. 19 is an exemplary method of measuring the muscular-skeletal system in accordance with an exemplary embodiment;

FIG. 20 is an exemplary method of a disposable orthopedic system in accordance with an exemplary embodiment; and FIG. 21 is an exemplary method of a disposable orthopedic system in accordance with an exemplary embodiment.

DETAILED DESCRIPTION

Figure 1:
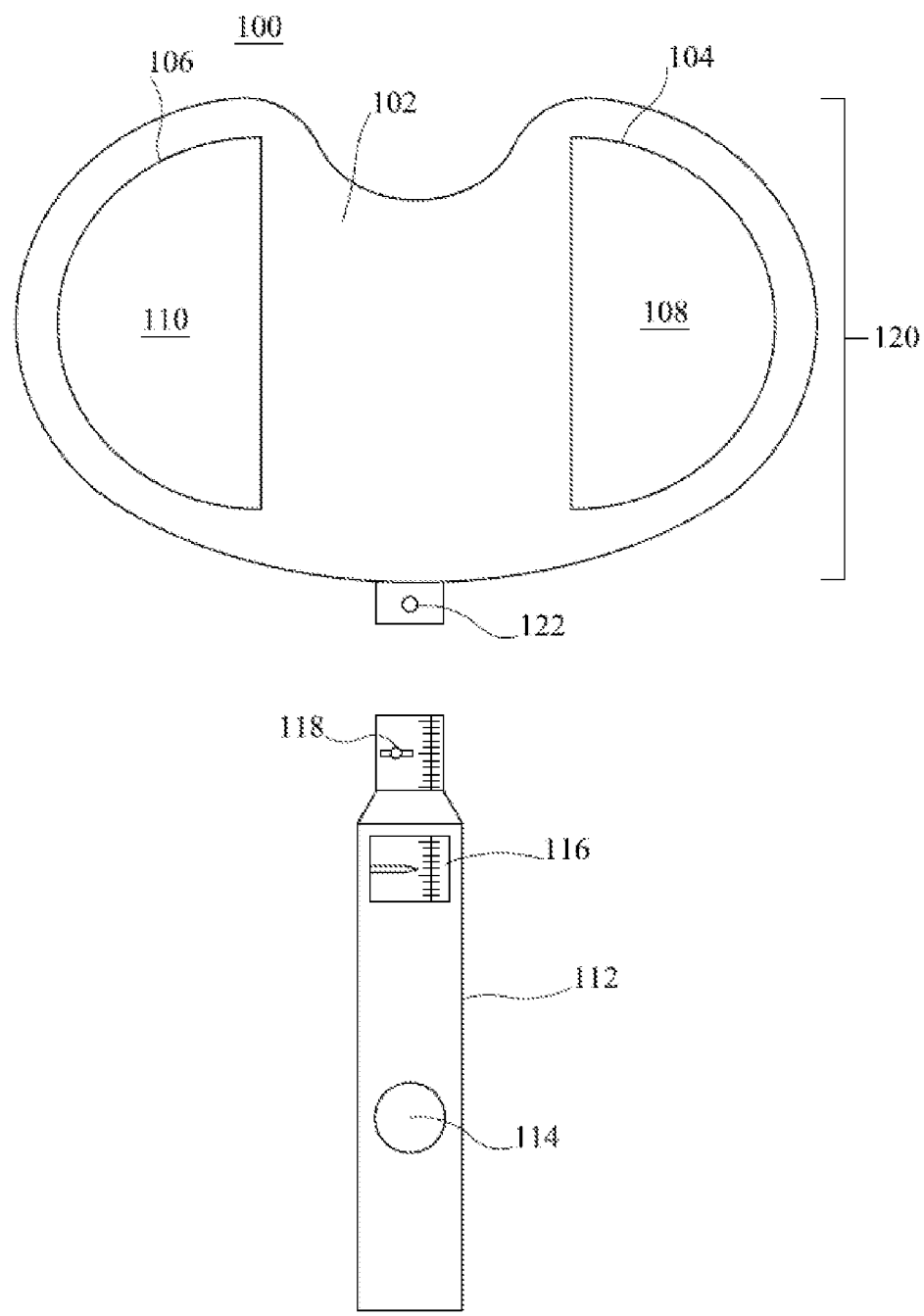
FIG. 1 is a top view of a dynamic distractor in accordance with an exemplary embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally, the sizes of structures used in exemplary embodiments are not limited by any discussion herein (e.g., the sizes of structures can be macro (centimeter, meter, and size), micro (micrometer), nanometer size and smaller).

Notice that similar reference numerals and letters refer to similar items in the following figures, and thus once an item is defined in one figure, it may not be discussed or further defined in the following figures.

In all of the examples illustrated and discussed herein, any specific values, should be interpreted to be illustrative only and non-limiting. Thus, other examples of the exemplary embodiments could have different values.

In general, successful orthopedic surgery including the implantation of an orthopedic device into the muscular-skeletal system depends on multiple factors. One factor is that the surgeon strives to maintain adequate alignment of the extremity or implanted device to the ideal. A second factor is proper seating of an implant for stability. A third factor is loading on the skeletal system or replacement implant. A fourth factor is alignment of implanted components in relation to one another. A fifth factor is balance of loading over a range motion.

By way of a device herein contemplated, the surgeon receives measured data during surgery and post operatively on the factors listed above. As one example, accurate measurements can be made during orthopedic surgery to determine if bones or an implant are optimally balanced and aligned. This can reduce operating time and surgical stress for both the surgeon and patient. The data generated by direct measurement can be further processed to assess long-term integrity based on maintaining surgical parameters within predetermined ranges. The measured data in conjunction with patient information can lead to improved design and materials.

FIG. 1 is a top view of a dynamic distractor 100 in accordance with an exemplary embodiment. Dynamic distractor 100 is also known as a dynamic spacer block. Dynamic distractor 100 is a sensored device that is used during surgery of a muscular-skeletal system. Dynamic distractor 100 can be used in conjunction with other tools common to orthopedic surgery as will be disclosed in more detail hereinbelow. In at least one exemplary embodiment, the system is used during orthopedic joint surgery and more specifically during implantation of an artificial joint. The system uses one or more sensors intra-operatively to define implant loading, positioning, achieve appropriate implant orientation, balance, and limb alignment. In particular, dynamic distractor combines the ability to align and measure one or more other parameters (e.g. load, blood flow, distance, etc. . . . ) that provides quantitative data to a surgeon that allows the orthopedic surgery to be measured and adjusted within predetermined values or ranges based on the measured data and a database of other similar procedures. The system is designed broadly for use on the skeletal system including but not limited to the spinal column, knee, hip, ankle, shoulder, wrist, articulating, and non-articulating structures.

Dynamic distractor 100 comprises an upper support structure and a lower support structure. An active or dynamic spacer portion 120 of dynamic spacer block comprises the upper and lower support structures. A lift mechanism (not shown) couples to an interior surface of upper support structure and an interior surface of the lower support structure. A handle 112 couples to the lift mechanism. In one embodiment, handle 112 is operatively coupled to the lift mechanism to change a gap of the spacer block. Handle 112 can also be used to guide dynamic distractor 100 between regions of the muscular-skeletal system. In general, the upper support structure has a superior surface 102 that interfaces with a surface of the muscular-skeletal system. Similarly, the lower support structure has an inferior surface that interfaces with a surface of the muscular-skeletal system.

In one embodiment, handle 112 can be rotated to adjust the lift mechanism to increase or decrease a gap between the superior and inferior surfaces of the active spacer block thereby modifying the height or thickness of dynamic distractor 100. In a non-limiting example to illustrate a disposable aspect, superior surface 102, the inferior surface, or both surfaces include at least one cavity or recess for housing at least one sensor module. The sensor module includes at least one sensor for measuring a parameter of the muscular-skeletal system. For example, the sensor can measure a force or pressure. As will be disclosed hereinbelow, the sensor can be disabled so it cannot be reused and disposed of after the procedure has been performed. In a further example, dynamic distractor 100 can be placed between two or more bone surfaces such that the superior surface 102 and the inferior surface contact surfaces of the muscular-skeletal system related to a joint. In one embodiment, the sensor is coupled to a surface of the muscular-skeletal system for measuring a parameter when positioned between surfaces. Handle 112 can be rotated to different gap heights allowing pressure measurements at the different gap heights to generate data of gap versus pressure.

Handle 112 further includes an opening 114, a decoupling mechanism 118, and a display 116. Opening 114 is used to receive additional components of the system that will be described in more detail hereinbelow. Decoupling mechanism 118 allows removal of the handle during parts of a surgery to allow access to the muscular-skeletal system. Decoupling mechanism 118 couples to a locking mechanism that locks handle 112 to a shaft of the lift mechanism. Decoupling mechanism 118 releases the locking mechanism thereby allowing handle 112 to be removed from dynamic distractor 100. In one embodiment, the locking mechanism is a pin or ball that fits into a corresponding feature 122 on the shaft of the lift mechanism. Decoupling mechanism 118 releases or frees the pin or ball from feature 1122 thereby allowing removal of handle 112. Alternatively, decoupling mechanism 118 can be a hinge or joint that allows handle 112 to move in a direction that allows greater access by the surgeon to an area where the spacer block portion of dynamic distractor 100 has been placed. The display 116 on handle 112 can provide a readout of the gap between the superior surface 102 and the inferior surface as handle 112 is rotated to adjust spacing.

In a non-limiting example, dynamic distractor 100 is adapted for use in artificial knee implant surgery. It should be noted that dynamic distractor 100 can be similarly adapted for other orthopedic surgery where both distraction and parameter measurement is beneficial. A knee implant is used merely as an example to illustrate how dynamic distractor 100 can be used in a surgical environment. In at least one exemplary embodiment, the superior surface 102 of dynamic distractor 100 includes a recess or cavity 104 and a second recess or cavity 106. In one embodiment, a sensor 108 and a sensor 110 are pre-sterilized in one or more packages. The packaging is opened prior to or during surgery within the surgical zone to maintain sterility. Sensors 108 and sensor 110 are shown respectively placed in cavities 104 and 106 for measuring a parameter that aids in the surgical procedure. In the knee example, sensors 108 and 110 include pressure sensors such as strain gauges, mechanical-electrical-machined (mems) sensors, diaphragm structures, mechanical sensors, or other pressure measuring devices. In one embodiment, a major exposed surface of sensors 108 and 110 is in contact with the muscular-skeletal system after insertion. Alternatively, one or more layers of material or portions of the muscular-skeletal system can be between sensors 108 and 110 such that the parameter can be measured or transferred through the intervening layers. A force or pressure applied to the exposed surfaces is measured by sensors 108 and 110 while the gap of the dynamic distractor is adjusted. Alternatively, the lift mechanism in conjunction with sensors 108 and 110 can be set to a predetermined pressure. The lift mechanism gap will increase until the predetermine pressure is reached. Thus, identifying a gap height or thickness of dynamic distractor 100 to achieve the predetermined pressure.

In at least one exemplary embodiment, sensors 108 and 110 are disposable devices. After measurements have been taken, sensors 108 and 110 can be removed and disposed of in an appropriate manner. Alternatively, the sensors 108 and 110 can be permanent or an integral part of the superior surface of dynamic distractor 100. The housing can be designed to be reused and to withstand a sterilization process after each use. The main body of dynamic distractor 100 as well as sensors 108 and 110 are cleaned and sterilized before each surgical usage.

Dynamic distractor 100 in a zero gap (or closed condition) is less than 8 millimeters thick for the knee application and can expand using the lift mechanism to greater than 25 millimeters. This range is sufficient for the majority of artificial knee implant surgeries being performed. The spacer portion 120 of dynamic distractor 100 contains the superior surface 102 and the inferior surface that articulates to at least two bone ends of the muscular-skeletal system. In the knee example, the dynamic distractor 100 is placed between the distal end of the femur and the proximal end of the tibia. As mentioned previously sensors 108 and 110 are in a housing. In one embodiment, the housing includes sensor elements to define the loads on the medial and lateral compartments. The sensored elements can comprise load displacement sensors, accelerometers, GPS locators, telemetry, power management circuitry, a power source and an ASIC.

As disclosed above, the spacer portion 120 of dynamic distractor 100 is placed between the femur and tibia in extension. The dynamic distractor 100 is configured with no gap (e.g. minimum height or thickness) or having a gap that can be inserted and removed without tissue damage. In general, the gap can be increased by rotating handle 112 after insertion such that the inferior surface of dynamic distractor 100 contacts a prepared surface of a proximal end of a tibia and the superior surface contacts the prepared distal end of the femur. In general, the femoral and tibial cuts in extension are made parallel to one another. Similarly, the femoral cut in flexion is made parallel to the prepared end of the tibia. The gap is measured to determine a combined thickness of the implants with the leg in extension. The prepared ends of the tibia and femur can be checked for alignment with the mechanical axis at this time as will be disclosed in detail below.

Typically, the surgeon selects the artificial components based on the cross-sectional size of the prepared bones. The variable component of the implant surgery is the final insert. The final insert has one or more bearing surfaces for interfacing with a femoral implant. In one embodiment, the measured gap height created by dynamic distractor 100 is used to define an insert thickness or height. The thickness of a final insert can change during surgery as further bone cuts or tissue tensioning occurs. Dynamic distractor 100 can be used during surgery to measure loading and gap height after each bone modification or after an orthopedic component has been implanted.

Dynamic distractor 100 can also be used to obtain an optimal balance. Balance is related to the measured loading between two or more areas. The measured values can than be adjusted to a predetermined relationship and within a predetermined value range. In the knee example, balance is associated with the differential pressure applied by each condyle on the bearing surfaces of the implant. Ideally, a predetermined surface area of the femoral implant condyle contacts the bearing surface to distribute the load and minimize wear. In a non-limiting example, a predetermined relationship between measured values by sensors 108 and 110 of dynamic distractor 100 is maintained after implantation of the artificial components. In one embodiment, the balance of the knee is maintained by having the measured load in each compartment approximately equal. A method to balance the loading of the compartments is through ligament release on the side having the larger loading value. Ligament release reduces loading primarily on the adjacent compartment. The loading can be read off a display on dynamic distractor 100 allowing the surgeon to view the change in loading and the differential value with each release. The lift mechanism provides sufficient room between the superior and inferior surfaces of dynamic distractor 100 for a surgeon to perform a release procedure without removing the device. A next greater thickness of an insert can be selected should the absolute loading value on each condyle fall outside the predetermined range due to the soft tissue release. Handle 112 can be rotated to increase the gap height to the next larger insert value to ensure the measured loading falls within the predetermined range and the differential loading falls within a predetermined range (after the soft tissue release).

The loading and balance of an implanted joint should be maintained within the predetermined values throughout the range of motion. In at least one exemplary embodiment, measurements are taken when the tibia is at a ninety-degree angle to the femur. Handle 112 is used to position the spacer block portion of distractor 100 between the femur and the tibia. The inferior surface of dynamic distractor 100 is in contact with the prepared surface of the tibia. In one embodiment, the superior surface 102 is in contact with the remaining portion of the condyles of the femur. Thus, the condyle surfaces of the femur are in contact with sensors 108 and 110 on the superior surface of dynamic distractor 100. In the example, a gap height of dynamic distractor 100 is reduced to accommodate the condyles that remain on the distal end of the femur in flexion. The gap height of dynamic distractor 100 can then be adjusted to a height corresponding to the gap height in extension less the thickness of the femoral implant whereby the leg in flexion is similar to the leg in extension.

The loading on sensors 108 and 110 with the leg in flexion can be measured. The measurement is of value if the condyles are not damaged or degraded. In one embodiment, soft tissue release is used to adjust the balance between compartments with the leg in flexion. The soft tissue release can also be performed later in the procedure after the femoral implant has been implanted. Similar to the leg in extension, soft tissue release is performed to reduce the tension on the side having the higher compartment reading with dynamic distractor 100 in place. After soft tissue release, the readings in each compartment should be within a predetermined differential range. The distal end of the femur can then be prepared for receiving the femoral implant, which removes the remaining portion of the condyles. As disclosed, the surface of the femur is prepared to be parallel to the prepared tibial surface in flexion. This can be achieved by specific ligament releases in flexion, and/or rotation of the femoral implant to achieve a parallel levels between the posterior femoral condyles and proximal tibia. A femoral sizer can be attached to the distractor to allow sizing of the femur, coupled with rotation of the femur. This allows dynamic rotation to obtain equally balanced flexion compartments.

In a non-limiting example, the femoral implant component can be temporarily attached to the distal end of the femur. Measurements can be taken throughout the entire three-dimensional range of motion using dynamic distractor 100 to ensure that the implanted knee operates similarly in all positions. A gap provided by dynamic distractor 100 would be adjusted to a combined thickness of the final insert thickness and the tibial implant thickness. Dynamic distractor 100 can incrementally increase or decrease the gap to allow the surgeon to determine how different insert thicknesses affect load and balance measurements. In one embodiment, accelerometers are used to provide position and relational positioning information. The data can be stored in memory for later use or displayed to provide instant feedback to the surgeon on the implant status. Further adjustments to load and balance can be made with dynamic distractor in place if desired over different positions within the range of motion. Although one implant sequence is disclosed, it is well known that surgeons have different approaches, methodologies and procedure sequences. The use of dynamic distractor 100 would be applied similarly to distract and measure in different relational positions with the device in place. Furthermore, the device can be used or modified for use on different parts of the anatomy of the muscular-skeletal system.

Figure 2:
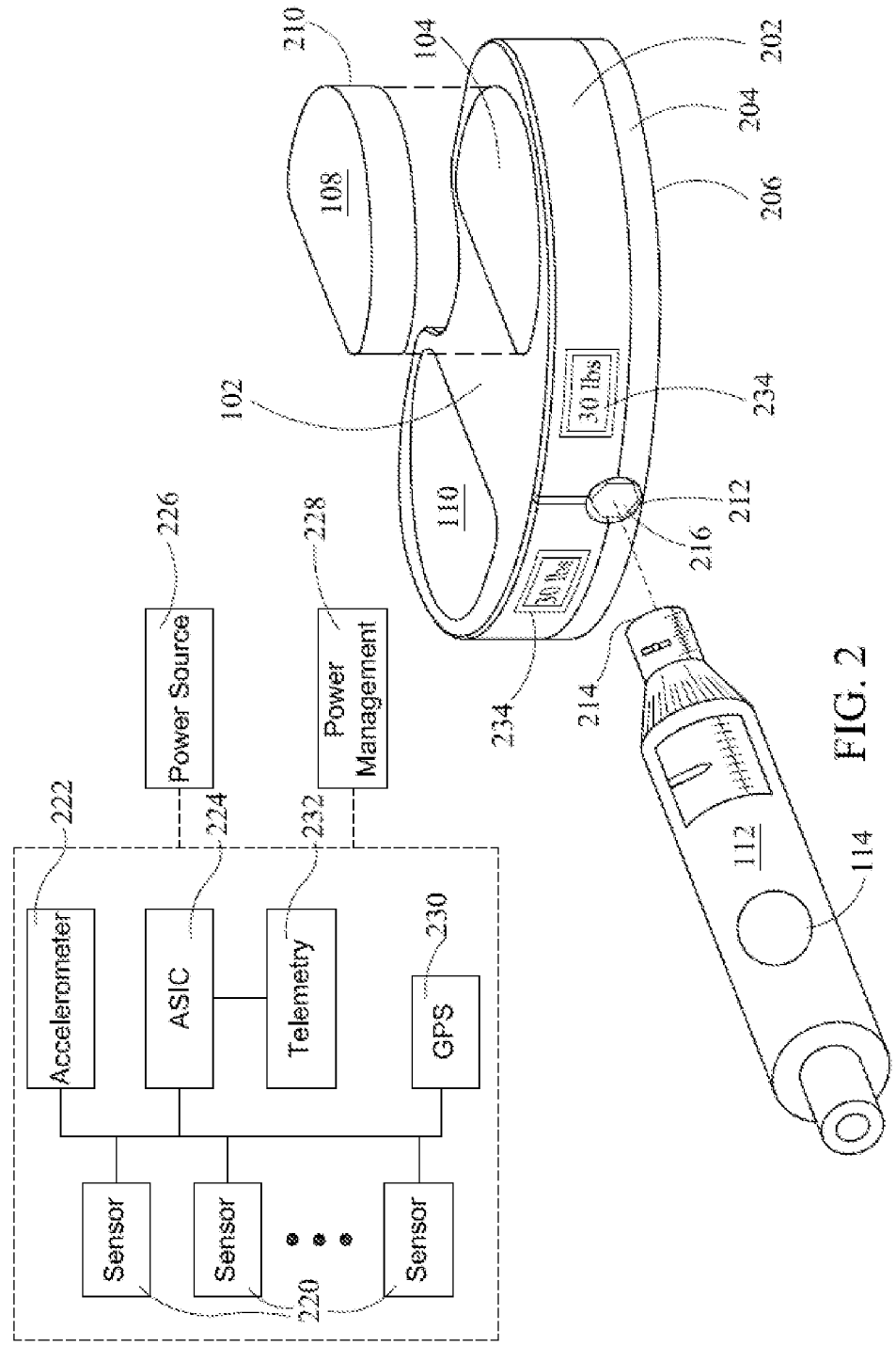
FIG. 2 is a side view of a dynamic distractor having a minimum height in accordance with an exemplary embodiment.

FIG. 2 is a side view of dynamic distractor 100 having a minimum height in accordance with an exemplary embodiment. Dynamic distractor comprises an upper support structure 202 having superior surface 102 and a lower support structure 204 having an inferior surface 206. In the example, upper support structure 202, the lift mechanism, and lower support structure 204 supports loading typical for a joint of the muscular-skeletal system. Upper and lower support structures 202 and 204 comprise a rigid and load bearing materials such as metals, composite materials, and plastics that will not flex under loading. In one embodiment, stainless steel is used in the manufacture of the lift mechanism and upper and lower support structures 204 and 202.

Dynamic distractor 100 is used to distract surfaces of the muscular-skeletal system. Dynamic distractor 100 can be used in an invasive procedure such as orthopedic surgery. In the non-limiting example, dynamic distractor 100 can distract surfaces of the muscular-skeletal system in a range of approximately 8 millimeters to 25 millimeters. The support surfaces of dynamic distractor 100 do not flex under loading of the muscular-skeletal system. In one embodiment, dynamic distractor 100 has a minimum height or thickness between support surfaces of less than 8 millimeters. In at least one application, a space between support structures 202 and 204 is provided when dynamic distractor 100 is opened to a height greater than the minimum height. The space between support structures 202 and 204 when opened allows a surgeon to perform soft tissue release with the device in place.

A cavity 104 is illustrated in superior surface 102 of upper support structure 202. The cavity 104 is shaped similarly to a housing 210 of sensor 108. Housing 210 is placed within cavity 108 for measuring a compressive force applied across superior surface 102 and inferior surface 206. In the knee example, a condyle (implanted or natural) couples to an exposed surface of sensor 108. A pressure or force applied to sensor 108 is measured and displayed by dynamic distractor 100. Sensor 110 is shown placed in its corresponding cavity in superior surface 102. In one embodiment, the exposed surfaces of sensors 108 and 110 are approximately planar to the superior surface 102. The exposed surface of sensor 108 and 110 can be flat or contoured. Sensors 108 and 110 can be removed from upper support structure 202 and disposed after the surgery has been performed. In one embodiment, a push rod is exposed in the interior surface of upper support structure 202 that when pressed can apply a force to housing 210 that removes sensor 108 from cavity 208

In one embodiment, housing 210 is formed of a plastic material. The sensor and electronic circuitry is fitted in housing 210. The electronic circuitry comprises one or more sensors 220, one or more accelerometers 222, an ASIC integrated circuit 224, a power source 226, power management circuitry 228, GPS circuitry 230, and telemetry 232. The power source 226 can be a battery or other temporary power source that is coupled to the electronic circuitry prior to surgery. The power source 226 has sufficient power to enable the circuitry for a period of time that will cover the vast majority of surgeries. The power management circuitry 228 works in conjunction with the power source to maximize the life of the power source by disabling system components when they are not being used. In general, an ASIC circuit controls and coordinates when sensing occurs, can store data to memory, and can transmit data in real time or collect and send data at a more appropriate time to a remote system for further processing. The ASIC includes multiple ports that couple to one or more sensors 220. The ASIC couples, to at least one sensor 220, at least one accelerometer 222, GPS 232, and telemetry circuitry 232. The ASIC 222 can include the integration of telemetry circuitry 232, power management circuitry 228, GPS circuitry 230, memory, and sensors 220 to further reduce the form factor of the sensing system. In the example, the at least one sensor 220 is a pressure sensor that is coupled to the exposed surface of the housing. The pressure sensor converts the pressure to an electrical signal that is received by the ASIC. The at least one accelerometer 222 and GPS 232 provides positioning information at the time of sensing. Telemetry circuitry 232 communicates through a wired or wireless path. In one embodiment, the data is sent to a remote processing unit that can process and display information for use by the surgeon or medical staff. One or more displays 234 can be placed on dynamic distractor 100 to simplify viewing of a pressure or force measured by sensors 108 and 110 thereby allowing real time loading and balance differential to be seen at a glance. The information can be stored in memory on the sensor or transmitted to a database for long-term storage and processing.

In a zero gap or minimum height condition, the lift mechanism is enclosed within the device. An opening 212 exposes a threaded rod 216 that is a component of the lift mechanism. The exposed end portion of threaded rod 216 is shaped for receiving handle 112. For example, a proximal end 214 of handle 212 is shown having a hexagonal opening that operatively couples to a hexagonal shaped end of threaded rod 216. The surfaces of the hexagonal surface mate with the surfaces of the threaded rod for distributing the torque required to rotate threaded rod 216 when increasing a gap between superior surface 102 and inferior surface 206 to distract surfaces of the muscular-skeletal system. Distributing the torque over a large surface area prevents stripping of either the hexagonal shaped opening of handle 212 or the hexagonal shaped exposed end of threaded rod 216 when the device is under load. In one embodiment, a release and locking mechanism fastens handle 112 to threaded rod 216. Pressing or sliding unlocking button 218 releases the locking mechanism to allow removal of handle 112.

Figure 3:
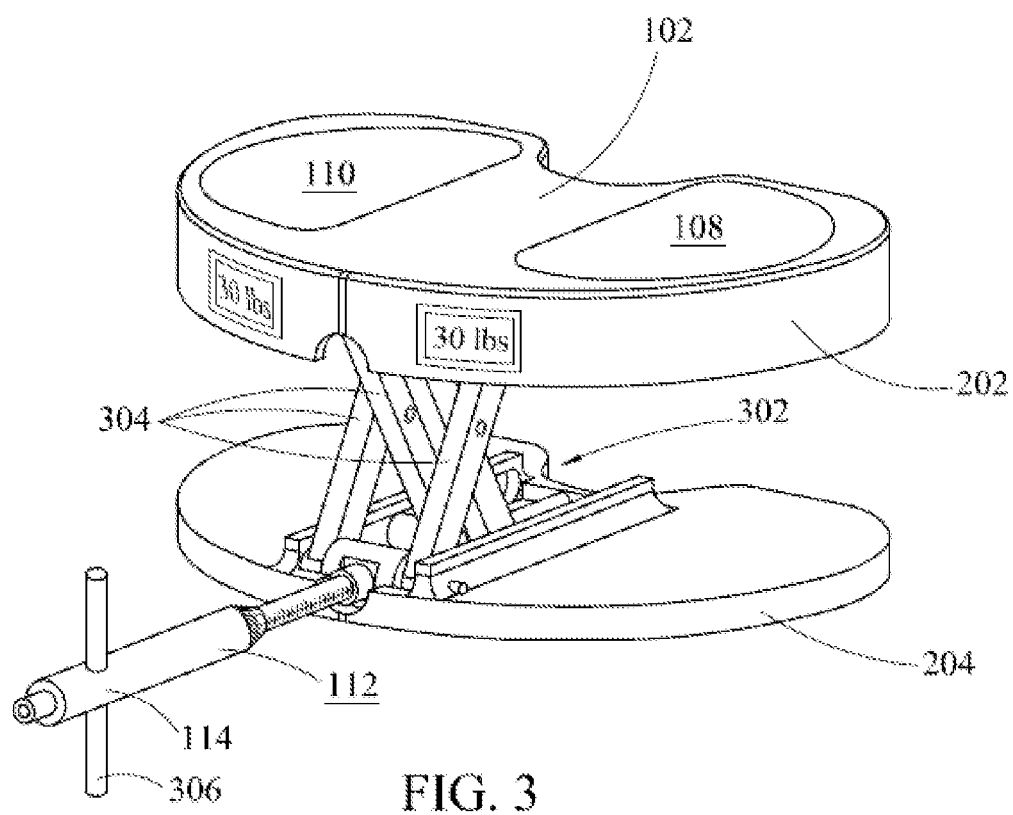
FIG. 3 is a view of a dynamic distractor opened for distracting two surfaces from each other in accordance with an exemplary embodiment.

FIG. 3 is a view of dynamic distractor 100 opened for distracting two surfaces of the muscular-skeletal system in accordance with an exemplary embodiment. A lift mechanism 302 comprises a scissor mechanism 304 for raising and lowering upper support structure 202 and lower support structure 204. In one embodiment, scissor mechanism 304 comprises more than one support structure each having a pivot. Scissor mechanism 304 is operatively coupled to an interior surface of upper support structure 202 and an interior surface of lower support structure 204. The structural beams are pinned to allow pivoting around the axis of attachment. The remaining beam-ends rest on the interior surfaces of either the upper and lower support structures 202 and 204. The beam-ends not fastened to the interior surfaces support upper and lower support structures 202 and 204 under load. Threaded rod 212 is operatively coupled between the beam-ends of scissor mechanism 304 corresponding to lower support structure 204. Rotating rod 212 can increase or decrease distance between beam ends of the scissor mechanism 204.

A rod 306 can be coupled to opening 114 of handle 112. The rod 306 can be used to reduce the torque needed to rotate threaded rod 212 in either direction under load. Increasing a distance between beam-ends of scissor mechanism 304 reduces the gap between superior surface 102 and inferior surface 206 as the two or more beams pivot around a centrally located axis. Conversely, decreasing a distance between beam-ends of scissor mechanism 304 increases the gap between superior surface 102 and inferior surface 206.

Figure 4:
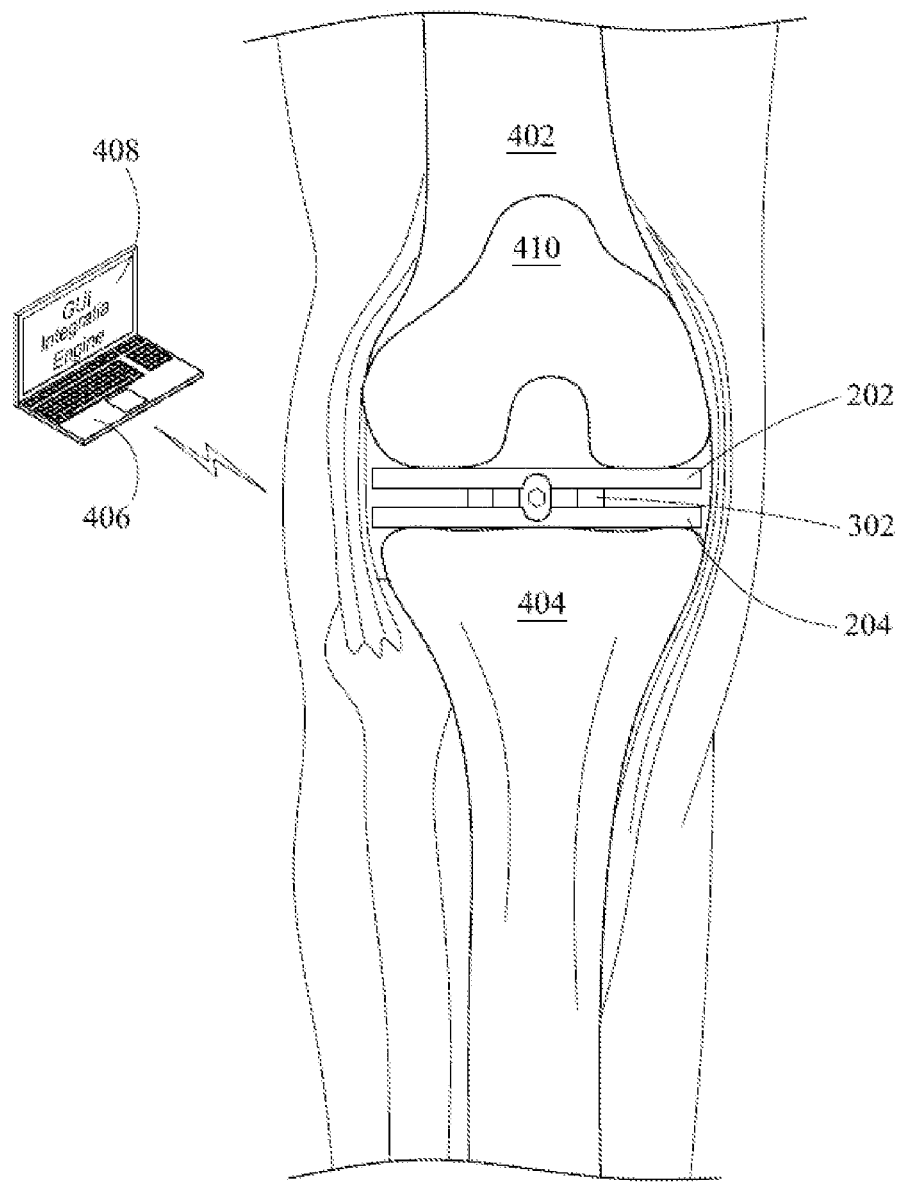
FIG. 4 is an anterior view of a dynamic distractor placed in a knee joint in accordance with an exemplary embodiment.

FIG. 4 is an anterior view of a dynamic distractor 100 placed in a knee joint in accordance with an exemplary embodiment. In the non-limiting example, a distal end of a femur 102 is shown having a femoral implant. The femoral implant has artificial condyles that contact sensors 108 and 110. The proximal end of a tibia 404 has been initially shaped for receiving a tibial implant. As is well known by one skilled in the art, a complete knee implant comprises the tibial implant, the femoral implant, and an insert that includes bearing surfaces that mate with the artificial condyle surfaces of the femoral implant. In one embodiment, dynamic distractor (100) includes an adjustable handle 112 that aids in the insertion of the spacer portion into a joint region of the muscular-skeletal system. For example, the spacer portion of dynamic distractor 100 is inserted into the knee joint using handle 112 but then rotated away from the patellar tendon, collapsed into the trail, or removed to allow the reduction of the patella to depict loads on the instrument. The thickness or height of the three components is contemplated for the bone surface preparation when using dynamic distractor 100. In one embodiment, the combined thickness of the femoral implant, final insert, and tibial implant is approximately 20 millimeters thick. Adjustments to the prepared bone surfaces and thickness of the insert are made during surgery using data provided by dynamic distractor 100 to ensure correct loading, balance, and alignment.

Sensors 108 and 110 include circuitry for communication with a processing unit 406. In one embodiment, data is sent wirelessly using a radio frequency communication standard such as Bluetooth, UWB, or Zigbee. The data can be encrypted to securely transmit the patient information and maintain patient privacy. In one embodiment, external processing unit 406 is in a notebook computer, personal computer, or custom equipment. For illustration purposes, external processing unit 406 is shown in a notebook computer that includes software and a GUI designed for the surgical application. The notebook computer has a display 408 that can be used by the medical staff during the operation to display real time measurement from dynamic distractor 100. The notebook computer is typically placed outside the surgical zone but within viewing range of the surgeon.

A substantial benefit of dynamic distractor 100 is in performing soft tissue release both in extension and in flexion. In extension, dynamic distractor 100 can be set to a height corresponding to an insert size. In one embodiment, manufacturers of an implantable joint will provide specifications for load, balance, and alignment once sufficient clinical data has been generated. The surgeon can also manipulate the leg to subjectively gauge the loading on the joint. The surgeon can adjust dynamic distractor 100 to increase or decrease the height or gap corresponding to a different thickness insert size until a desired loading is achieved. A substantial imbalance corresponds to a differential loading measured by sensors 108 and 110 outside a predetermined range. The loading measured by sensors 108 and 110 should be approximately equal in each compartment. The data provided by sensors 108 and 110 can be used to provide a solution to the surgeon. For example, data from sensors 108 and 110 is sent wirelessly to processing unit 406. The data indicates a substantial differential pressure between measurements from sensors 108 and 110 (e.g. imbalance). In one embodiment, the data can be processed and displayed on display 408 with suggestions for the removal of material from the tibial surface to reduce the differential reading. The suggestion can include where material should be removed and how much material is removed from the tibial surface. Alternatively, the assessment of the loading and differential between compartments can indicate that soft tissue release is sufficient to bring the joint within predetermined ranges for absolute load and balance.

A further benefit of dynamic distractor 100 is in soft tissue release to modify loading measured by sensors 108 and 110 and the differential (e.g. balance) between the measured values in each compartment. Dynamic distractor 100 remains in place while soft tissue release is being performed allowing for real time measurement and modification to occur. The feedback to the surgeon is immediate as the soft tissue cuts are made. Two issues are resolved by dynamic distractor 100. An open area formed between the interior surfaces of upper support structure 202 and lower support structure 204 under distraction provides surgical access. In most cases, the gap is sufficient to allow a scalpel or blade access to the lateral or medial ligaments for soft tissue release in the gap or peripheral to dynamic distractor 100. In general, soft tissue release requires anterior access to the joint space. Handle 112 of dynamic distractor 100 can be removed providing further anterior access to the joint. Alternatively, handle 112 is hinged or includes a joint allowing it to be positioned away from the surgical area. Thus, dynamic distractor 100 enables soft tissue release by the surgeon to adjust the absolute loading measured by sensors 108 and 110 in each compartment to be within a predetermined range and to adjust the difference in compartment loadings within a predetermined range without removing the device.

Figure 5:
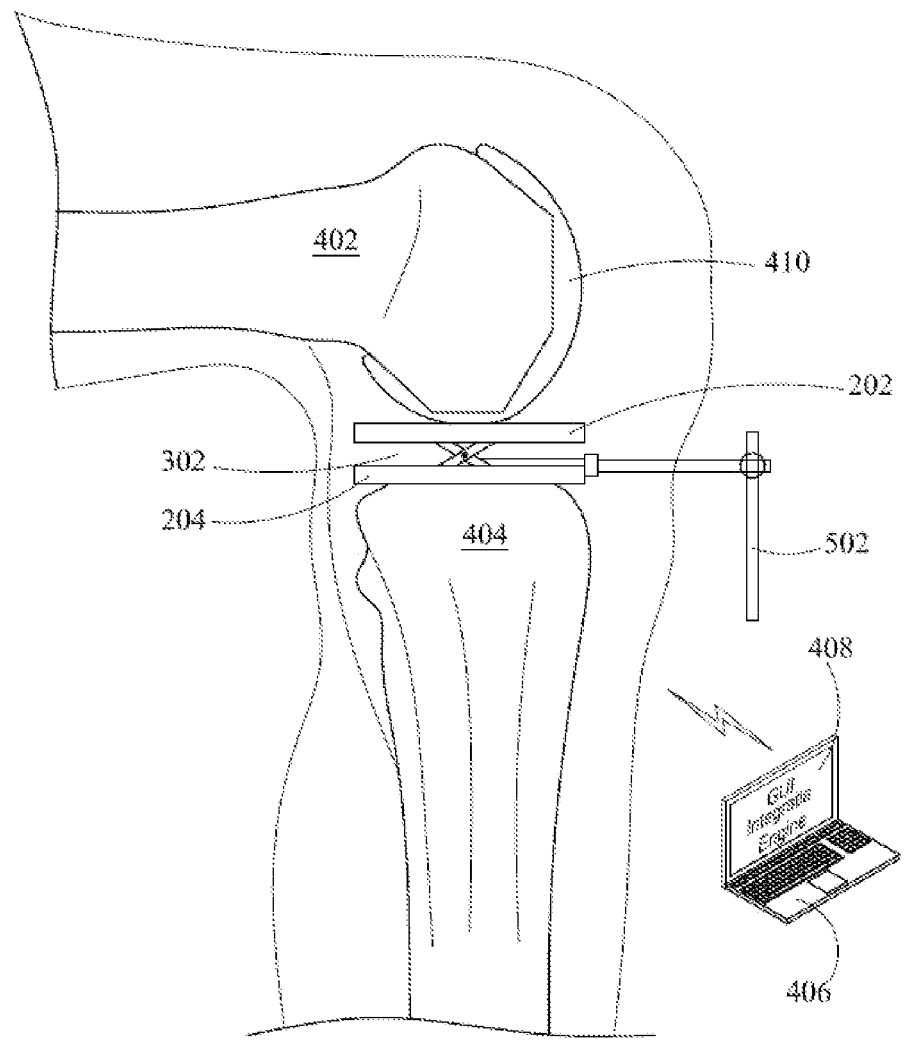
FIG. 5 is a lateral view of dynamic distractor in a knee joint positioned in flexion in accordance with an exemplary embodiment.

FIG. 5 is a lateral view of dynamic distractor 100 in a knee joint positioned in flexion in accordance with an exemplary embodiment. In a non-limiting example, load and balance measurements are performed using dynamic distractor 100 with the leg in at least two positions (e.g. the leg in extension and the leg in flexion). For example, measurements are taken in extension as disclosed hereinabove and in flexion with the leg positioned having femur 402 forming a 90 degree angle to tibia 404. In one embodiment, accelerometers in sensors 108 and 110 are used to determine relative positioning of the femur and tibia to one another. Under user control, measurements are taken at several points over the range of motion with dynamic distractor 100 in place thereby substantially simplifying a data collection process. Measurements over the range of motion can be taken when the femoral implant has been installed or if the distal femur has not been modified. Alternatively, dynamic distractor 100 can be reduced in height by rotating handle 112 until there is sufficient room to move the leg to a new position and then increasing the height of distractor 100 to create the appropriate gap.

A drop alignment rod 502 is placed through opening 114 of handle 112. Drop alignment rod 502 is a visual aid for the surgeon to ensure that the leg is aligned adequately when the load and balance measurements are taken. Drop alignment rod 502 is used in conjunction with a knowledge of the leg mechanical axis or with markers placed on the patient to check alignment. The surgeon aligns alignment rod 502 to the leg mechanical axis and makes a subjective determination that the leg is correctly positioned. The surgeon can increase accuracy by pre-identifying points on the mechanical axis. The surgeon has the option of making adjustments if drop alignment rod 502 indicates a potential positional error. Drop alignment rod 502 can be tapered having a section with a greater width than opening 114 to retain it in place and prevent it from falling through. Other embodiments to retain drop alignment rod 502 can also be used.

Alternatively, drop alignment rod 502 can be a smart alignment aid for the surgeon that incorporates electronics similar to that described in FIG. 2. In general, drop alignment rod includes sensors to allow depiction of the mechanical axis. For example, drop alignment rod 502 can incorporate sensors to identify position in three-dimensional space. The electronics would allow drop alignment rod 502 to communicate with pre-operative defined locations or locations that are identified at the time of surgery using locator electronics. The drop rod can house light emitters to depict an axis as will be discussed in more detail hereinbelow. The electronics can include communication to external processing unit 406 with a graphic user interface that has the mechanical axis loaded therein.

Figure 6:
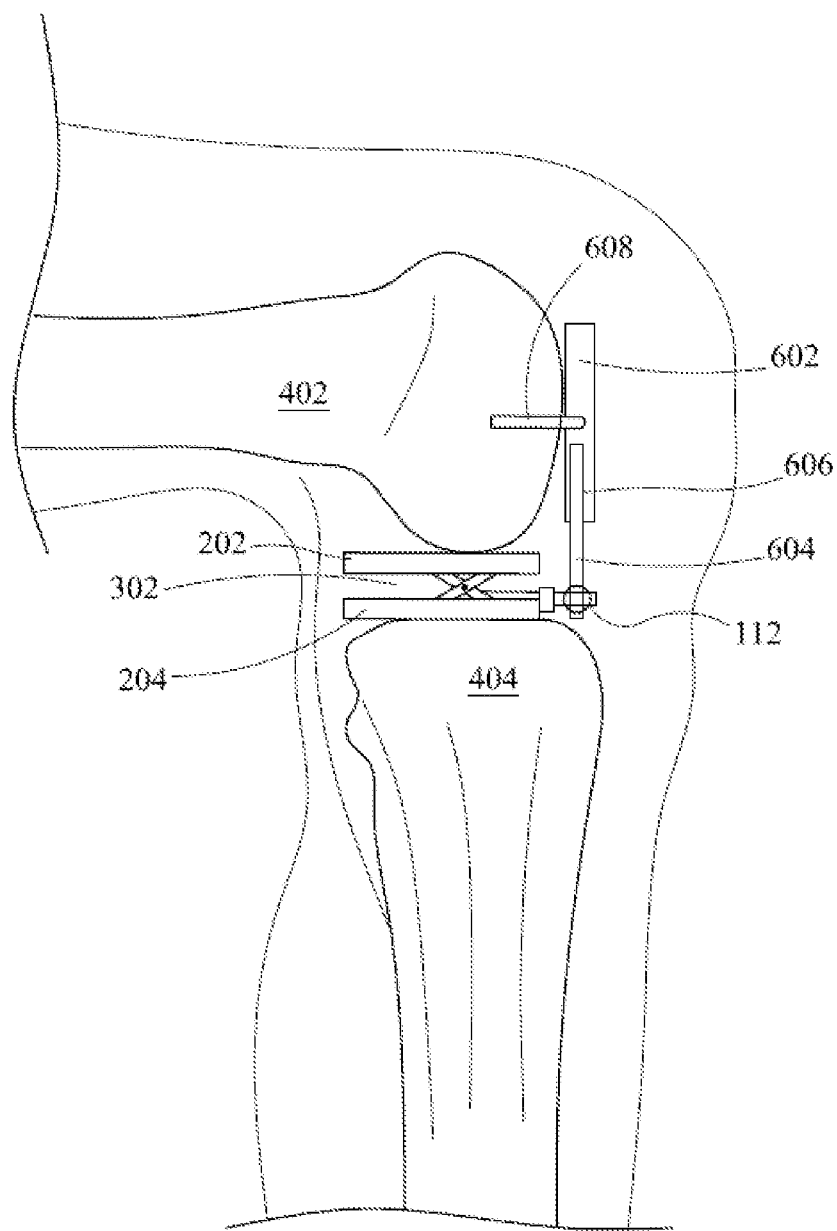
FIG. 6 is a lateral view of a dynamic distractor in a knee joint coupled to a cutting block in accordance with an exemplary embodiment.

FIG. 6 is a lateral view of a dynamic distractor 100 in a knee joint coupled to a cutting block 602 in accordance with an exemplary embodiment. In general, the surgeon utilizes surgical tools to obtain appropriate bony cuts to the skeletal system. The surgical tools are often mechanical devices used to achieve gross alignment of the skeletal system prior to or during an implant surgery. In the knee example, mechanical alignment aids are often used during orthopedic surgery to check alignment of the bony cuts of the femur and tibia to the mechanical axis of the leg. The mechanical alignment aids are not integrated together, take time to deploy, and have limited accuracy. Dynamic distractor 100 in concert with cutting block 602 is an integrated system for achieving alignment that can greatly reduce set up time thereby minimizing stress on the patient.

As illustrated, the leg is in flexion having a relational position of 90 degrees between femur 402 and tibia 404. A femoral rod 608 is coupled through the intermedullary canal of femur 402. A cutting block 602 is attached to the femoral rod 608 for shaping a portion of the surface of the distal end of femur 402 for receiving a femoral implant. Knee replacement surgery entails cutting bone a certain thickness and implanting a prosthesis to allow pain relief and motion. During the surgery, instruments are used to assist the surgeon in performing the surgical steps appropriately. Dynamic distractor 100 aids the surgeon by allowing quantitative measurement of the gap and parameter measurement during all stages of the procedure. For the knee, the data can supplement a surgeon's "feel" by providing data on absolute loading in each compartment, the load differential between compartments, positional information, and alignment information.

The portion of the surface of the distal end of femur 402 in contact with dynamic distractor 100 is shaped in a subsequent step. In a non-limiting example, the portion of the condyles in contact with superior surface 102, sensor 108, and sensor 110 are the natural condyles of the femur. The portion of the distal end of femur 402 being shaped corresponds to the condyle portion that would be in contact with the final spacer while the leg is in extension and partially through the range of motion. In at least one exemplary embodiment, an uprod 604 of dynamic distractor 100 couples to cutting block 602. Uprod 604 aids in the alignment of the cutting block 602 to dynamic distractor 100 and tibia 404. Uprod 604 further stabilizes cutting block 602 to prevent movement as the distal end of femur 402 is shaped.

In one embodiment, handle 112 is removed and an uprod 604 is attached to threaded rod 212. The uprod 604 can include a hinge that positions rod 604 vertically to mate with cutting block 602. Alternatively, handle 112 can include a hinge. In this example, handle 112 is uprod 604 and is inserted into cutting block 602. Furthermore, uprod 604 can be fastened or coupled to an opening or feature in handle 112 to couple to cutting block 602. In general, uprod 604 is placed at a right angle to the inferior surface of lower support structure 204 of dynamic distractor 100. In a prior step, the leg alignment can be checked to ensure it is within a predetermined range of the mechanical axis. In one embodiment, uprod 604 aligns approximately to the mechanical axis to secure cutting block 602 in an appropriate geometric orientation. Cutting block 602 includes a channel 606 for receiving uprod 604. Uprod 604 can be adjustable in length that simplifies insertion. As previously mentioned, uprod 604 is attached to dynamic distractor 100 to align with the mechanical axis of the leg corresponding to tibia 404. Fitted in the opening and into channel 606, uprod 604 maintains a positional relationship between cutting block 602, dynamic spacer block 100, femur 402, and tibia 404. More specifically, the proximal surface of tibia 404 is aligned to the mechanical axis thereby fixing the position of femur 402 and cutting block 602 in a similar fixed geometric relational position. Thus, the distal end of femur 402 is cut having surfaces parallel to the proximal tibial surface by coupling dynamic distractor 100 to cutting block 602 through uprod 604.

Figure 7:
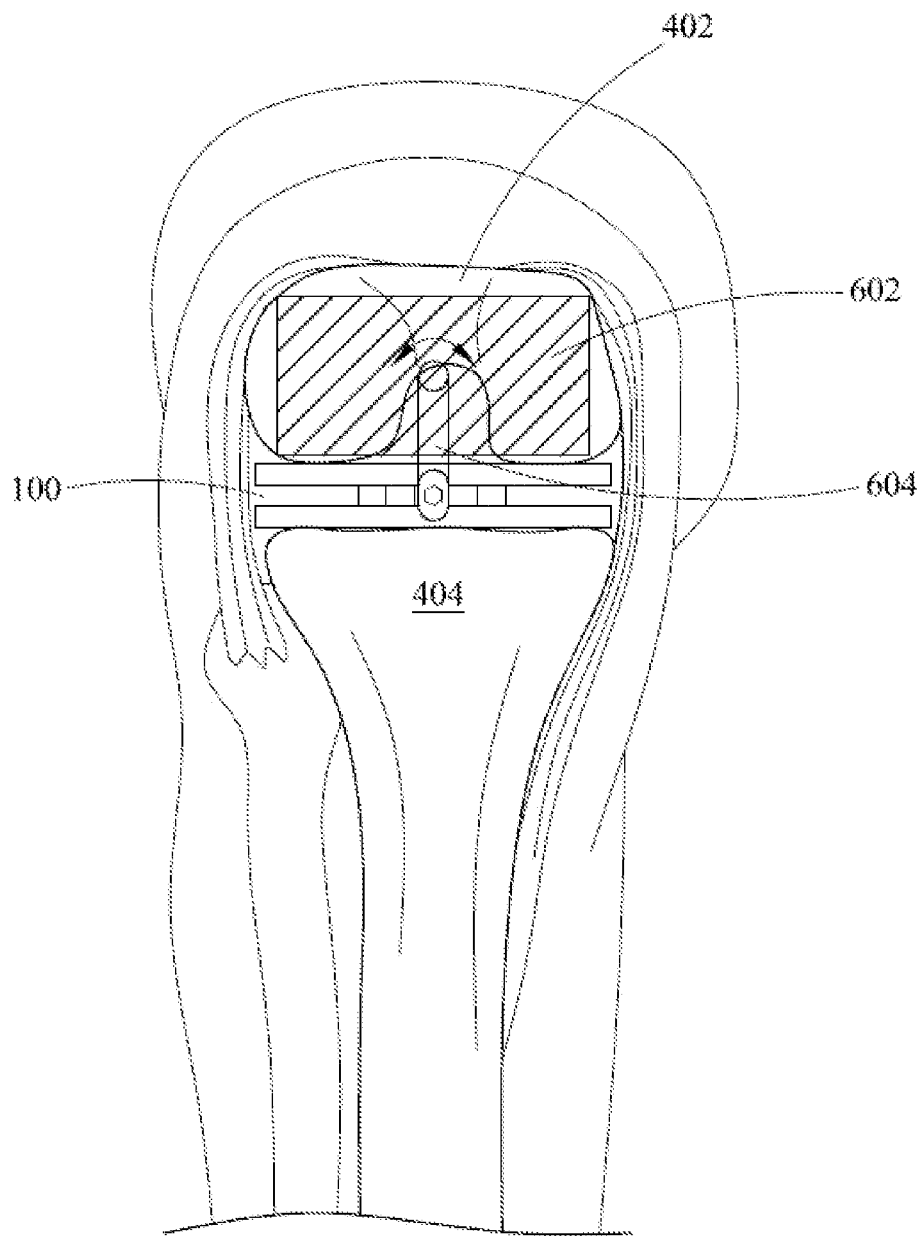
FIG. 7 is an anterior view of a cutting block coupled to dynamic distractor in accordance with an exemplary embodiment.

FIG. 7 is an anterior view of a cutting block 602 coupled to dynamic distractor 100 in accordance with an exemplary embodiment. Cutting block 602 is attached to the distal end of femur 402. Femoral rod 608 extends through cutting block 602 into the intermedullary canal. Uprod 604 is shown extending vertically into channel 606 of cutting block 602. In combination, femoral rod 608 and uprod 604 prevent movement and maintain alignment of the cutting block to the leg mechanical axis. As shown, cutting block 602 is illustrated as rectangular in shape. Cutting block 602 is shaped to form a predetermined bone shape on the distal end of femur 402 for receiving a femoral implant. Thus, the shape of cutting block 602 can vary significantly from that shown depending on the implant. The size of the cutting block 602 corresponds to the distal end size and the femoral implant selected by the surgeon. The surgeon uses a bone saw to remove portions of the distal end of femur 402 in conjunction with cutting block 602. In general, the cutting block 602 acts as a template to guide the bone saw and to cut the distal end of the femur in a predetermined geometric shape. As disclosed previously in the example, the portion of the distal end of femur 404 that is shaped corresponds to the contact portion of the condyles when the leg is in full extension and partially in flexion (e.g. <90 degrees). As mentioned previously, the portion of the distal end of femur 402 in contact the superior surface 102 of dynamic distractor 100 is shaped in a subsequent step.

Figure 8:
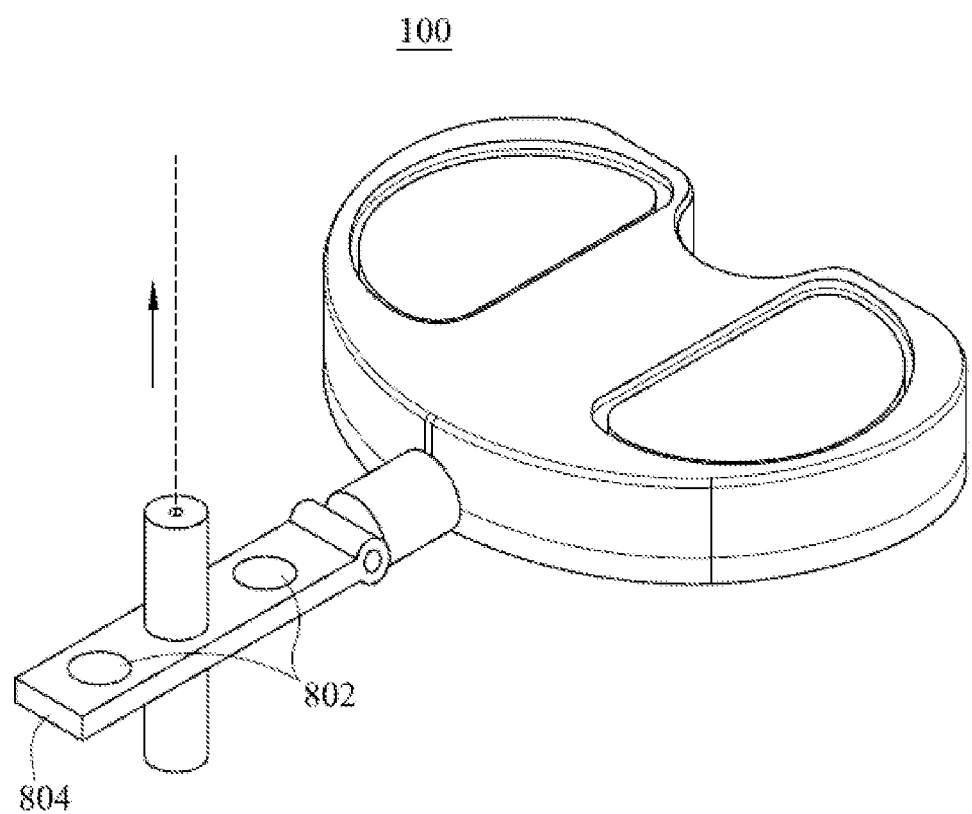
FIG. 8 is an illustration of dynamic distractor including alignment in accordance with an exemplary embodiment.

FIG. 8 is an illustration of dynamic distractor 100 including alignment in accordance with an exemplary embodiment. Dynamic distractor 100 includes one or more recesses 802 in a handle 804 for receiving an alignment aid to align a leg along the mechanical axis. In one embodiment, handle 804 can be handle 112 that includes recesses 802. Alternatively, handle 804 is a separate handle for dynamic distractor 100. Prior to checking alignment, handle 112 is removed from dynamic distractor 100. Handle 804 is coupled to threaded rod 212.

Initial bony cuts are made in alignment with the mechanical axis of the leg. In the knee example, the alignment aid is used to check that the femur and the tibia are correctly oriented prior to cutting. The surfaces of the bones are cut in alignment to the mechanical axis using a jig. Thus, the cut surfaces on the distal end of the femur and the proximal end of the tibia are aligned and can be used as a reference surfaces during the procedure. Alternatively, the alignment aid can be used to verify alignment throughout the procedure. Recesses 802 can be thru-holes in handle 804. In a non-limiting example, the alignment aid is one or more lasers 808. Lasers 808 are used to point along the mechanical axis of the leg. In one embodiment, lasers 808 are used to check alignment of the leg. A first laser is used to point in the direction of the hip joint. A second laser is used to point towards the ankle. In one embodiment, the first and second lasers are integrated into a single body. Handle 804 further comprises a hinge 806 to change the angle at which lasers 808 are directed. The housing of lasers 808 includes a power source such as a battery to generate the monochromatic light beam. The housing fits within one of recesses 802 or a thru-hole. Lasers 808 can be a disposable item that is discarded after the surgery is completed.

FIG. 9 is a side view of a leg in extension with dynamic distractor 100 in the knee joint region in accordance with an exemplary embodiment. The mechanical axis of the leg is approximately a straight line from the center of the femoral head through the knee joint and extending to the middle of the ankle joint. In a correctly aligned knee joint, the mechanical axis will pass approximately through the center of the knee joint. Alignment can be checked when dynamic distractor 100 is positioned in the knee joint region. As illustrated, the leg is in extension with handle 804 extending vertically from the knee joint region. In one embodiment, a target 902 is placed in an ankle or toe region of the foot in a path corresponding to center of the ankle on the mechanical axis of the leg. Similarly, a target 904 is placed in a path corresponding to the center of the head of the femur on the mechanical axis of the leg. Targets 902 are placed at a height similar to that of lasers 808. Lasers 808 are installed in the handle with one pointing in the direction of the hip joint and another pointing in the direction of the ankle joint. From the top view, lasers 808 send out a beam of light from a position that corresponds to the center of the knee. In one embodiment, the direction of the beam from lasers 808 is directed perpendicular to a plane of the prepared surface of the proximal end of the tibia.

Lasers 808 are directed perpendicular to the inferior surface of dynamic distractor 100. The placement of dynamic distractor 100 on the prepared tibial surface is such that handle 804 extends vertically at a point corresponding to the center of the knee joint. The leg is aligned correctly when the beams from lasers 808 hit the target at the points corresponding to the center of the head of the femur and the center of the ankle. Lasers 808 are positioned to align with the center of the knee joint. The surgeon can make adjustments to the bone surfaces or utilize soft tissue release to achieve alignment with the leg mechanical axis when lasers 808 are misaligned to the target. The system can be used to give a subjective or a measured determination on leg alignment in relation to a vargus or valgus alignment. The direction of misalignment in viewing targets 902 and 904 will dictate the type of correction and how much correction needs to be made. In an alternate embodiment, lasers 808 can be aimed such that the beam is viewable along the leg in a region by the center of the femoral head and the center of the angle. The surgeon can use this as a subjective visual gauge to determine if the leg is in alignment to the mechanical axis and respond appropriately, depending on what is viewed.

FIG. 10 is a top view of a leg in extension with dynamic distractor 100 in the knee joint area in accordance with an exemplary embodiment. Dynamic distractor 100 can measure spacing between the distal end of the femur and the tibia, loading in each compartment, and differential loading between compartments. The data can be sent to a processing unit and display as disclosed hereinabove. As mentioned previously, the mechanical axis of the leg corresponds to a straight line from the center of the ankle, through the center of the knee, and the center of the femoral head. Targets 902 and 904 are respectively located overlying the mechanical axis in an area local to the ankle and the hip regions. Targets 902 and 904 can include a fixture such as a strap, brace, or jig to hold the targets temporarily along the mechanical axis. Lasers 808 are enabled and placed in handle 804. The figure illustrates that targets 902 and 904 are on approximately the same plane as beams emitted by lasers 808 such that the beams impinge on a target unless grossly misaligned. Targets 902 and 904 can include calibration markings to indicate a measure of the misalignment. Alternatively, handle 804 is hinged allowing adjustment of the angle at which the beam from lasers 808 is directed. The direction of the lasers 808 corresponds to the plane of the bone cuts for the implant and the balance of the joint. Thus, the surgeon using a single device has both quantitative and subjective data relating to alignment to the mechanical axis, loading, balance, leg position, and gap measurement that allows gross/fine tuning during surgery that results in more consistent orthopedic outcomes.

Figure 11:
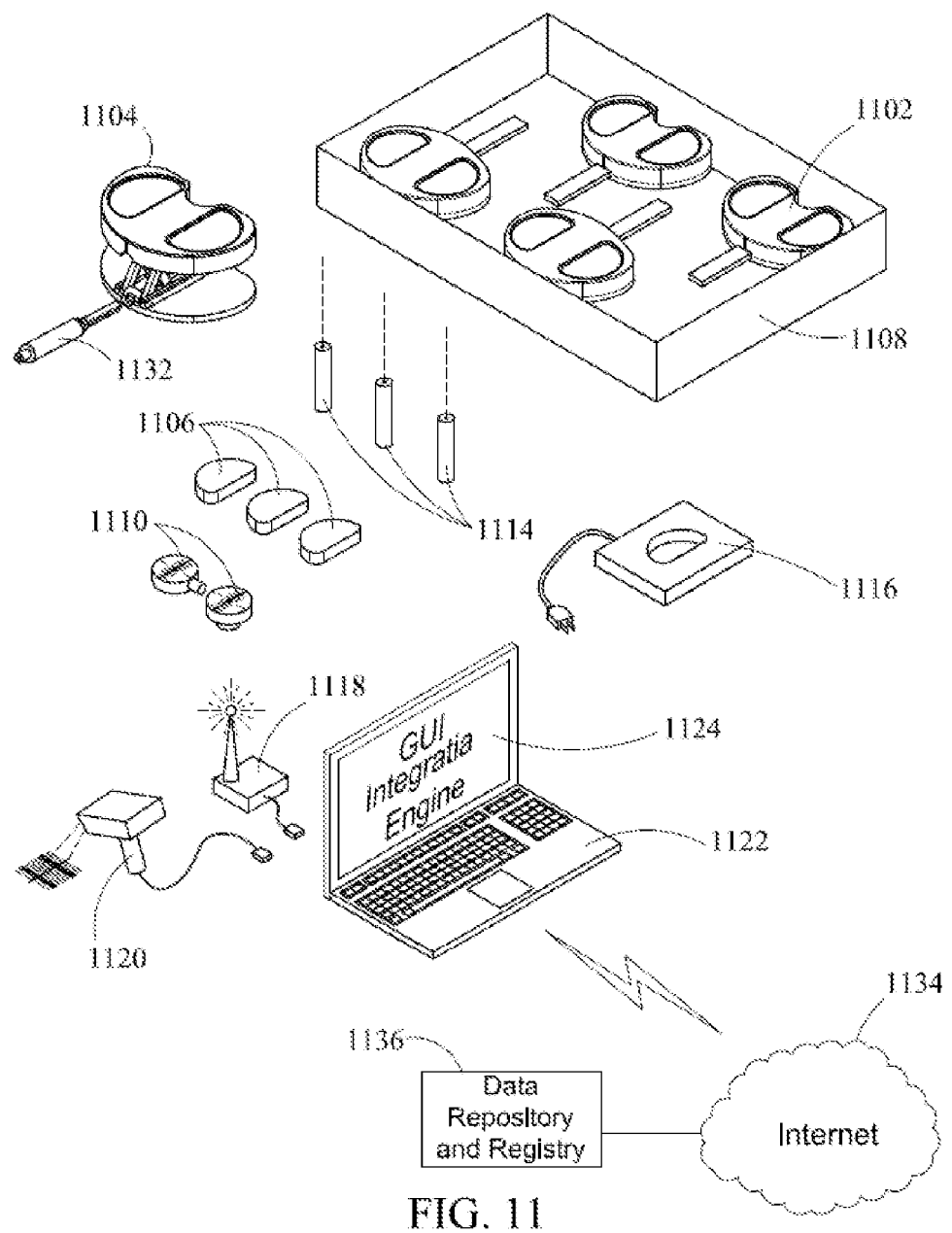
FIG. 11 is an illustration of a system for measuring one or more parameters of a biological life form in accordance with an exemplary embodiment.

FIG. 11 is an illustration of a system 1100 for measuring one or more parameters of a biological life form in accordance with an exemplary embodiment. In a non-limiting example, the system provides real time measurement capability to a surgeon of one or more parameters needed to assess a muscular-skeletal system. System 1100 comprises a plurality of spacer blocks 1102, a distractor 1104, sensors 1106, targets 1110, lasers 1114, a charger 1116, a receiver 1118, a reader 1120, a processing unit 1122, a display 1124 a drop rod 1126, an uprod 1128, a cutting block 1130, a handle 1132, a dynamic data repository and registry 1134. The system is adaptable to provide accurate measurements of parameters such as distance, weight, strain, pressure, wear, vibration, viscosity, and density to name but a few. In one embodiment, system 1100 is used in orthopedic surgery and more specifically to provide intra-operative measurement during joint implant surgery. System 1100 is adapted for orthopedic surgery and more specifically for knee surgery to illustrate operation of the system.

In general, system 1100 provides alignment and parameter measurement system for providing quantitative measurement of the muscular-skeletal system. In one embodiment, system 1100 is integrated with tools commonly used in orthopedics to reduce an adoption cycle to utilize new technology. System 1100 replaces standalone equipment or dedicated equipment that is used only for a small number of procedures that justifies the extra time and set up required to use this type of equipment. Furthermore, it is well known, that dedicated equipment can cost hundreds of thousands or millions of dollars for a single device. Many hospitals and other healthcare facilities cannot afford the high capital cost of these types of systems. Moreover, specialized equipment such as robotic systems or alignment systems for orthopedic surgery typically has a large footprint. The large footprint creates space and cost issues. The equipment must be stored, set up, calibrated, placed in the operating room, and then removed.

Conversely, measurement and alignment components of system 1100 are low cost disposables that make the measurement technology more accessible to the general public. There is no significant capital investment required to use the system. Moreover, payback begins immediately with use in providing quantitative information related to procedures thereby allowing analysis of outcomes based how the parameters being measured affect the procedure being measured. The data is used to initiate predetermined specifications for the procedure that can be measured and adjusted during the course of the procedure thereby optimizing the outcomes and reducing revisions. As mentioned previously, system 1100 can be used or integrated with tools that the majority of orthopedic surgeons have substantial experience or familiarity using on a regular basis. In one embodiment, sensors 1106 are placed in a spacer that separates two surfaces of the muscular-skeletal system. In a non-limiting example, the spacer can be spacer blocks 1102 or distractor 1104. A measurement of the parameter is taken after the spacer is inserted between at least two surfaces of the muscular-skeletal system. Sensors 1106 are in communication with processing unit 1122. In one embodiment, the processing unit 1122 is outside the sterile field and includes display 1124 and a GUI to provide the data in real time to the surgeon. Thus, the learning cycle can be very short to provide real time quantitative feedback to the surgeon as well as storing the data for subsequent use.

In a non-limiting example a spacer separates two surfaces of the muscular-skeletal system. The spacer has an inferior surface and a superior surface that contact the two surfaces. The spacer can have a fixed height or can have a variable height. The fixed height spacer is known as spacer blocks 1102. Each spacer block 1102 has a different thickness. The variable height spacer is known as the distractor 1104. The surface area of spacer blocks 1102 and distractor 1104 that couple to the surfaces of the muscular-skeletal system can also be provided in different sizes. The handle 1132 extends from the spacer and typically resides outside or beyond the two surface regions. The handle 1132 is used to direct the spacer between the two surfaces. In one embodiment, the handle 1132 operatively couples to a lift mechanism of the distractor 1104 to increase and decrease a gap between the superior and inferior surfaces of the spacer. The spacer and handle 1132 is part of system 1100 to measure alignment of the muscular-skeletal system. In one embodiment, at least one of the surfaces of the muscular-skeletal system that contacts the spacer has an optimal alignment to a mechanical axis of the muscular-skeletal system. The system measures the surface to mechanical axis alignment. In a non-limiting example, the misalignment can be corrected by a surgeon when the surface is misaligned to the mechanical axis outside a predetermined range as disclosed below.

Knee replacement surgery entails cutting bone having a predetermined spacing and implanting a prosthesis to allow pain relief and motion. During the surgery, instruments are used to assist the surgeon in performing the surgical steps appropriately. The majority of surgeons continue to use passive spacers to aid in defining the gaps between the cut bones. The thickness of the final insert is selected after placing one or more trial inserts in the artificial joint implant. The determination of whether the implanted components are correctly installed is still to a large extent by "feel" of the surgeon through movement of the leg. In general, spacer blocks 1102 and distractor 1104 of system 1100 is a spacer having an inferior and superior surface that separate at least two surfaces of the muscular-skeletal system. In the knee example, the inferior and superior surfaces are inserted between the femur and tibia of the knee. At least one of the inferior or superior surfaces of spacer blocks 1102 and distractor 1104 have a cavity or recess for receiving sensors 1106. In one embodiment, the cavity is on the superior surface of spacer blocks 1102 and distractor 1104. A gap between the surfaces of distractor 1104 is adjustable as described hereinabove. Tray 1108 includes multiple spacer blocks 1102 each having a different thickness. Thus, spacer blocks 1102 and distractor 1104 provide the surgeon with more than one option to measure spacing, alignment, and loading during the procedure. A benefit of the system is the familiarity that the surgeon will have with using similar type devices thereby reducing the learning curve to utilize system 1100. Furthermore, system 1100 can comprise spacer blocks 1102 and distractor 1104 having spacer blocks having different sized superior and inferior surface areas to more readily accommodate different bone shapes and sizes.

In general, a rectangle is formed by the bony cuts during surgery. The imaginary rectangle is formed between the cut distal end of a femur and the cut proximal end of tibia in extension and in conjunction with the mechanical axis of the lower leg. The prepared surfaces of the femur and tibia are shaped to respectively receive a femoral implant and a tibial implant. The femoral and tibial surfaces are parallel to one another when the leg is in extension and in flexion at 90 degrees. A predetermined width of the rectangle is the spacing between the planar surface cuts on femur and tibia. The predetermined width corresponds to the thickness of the combined orthopedic implant device comprising the femoral implant, an insert, and the tibial implant. A target thickness for the initial cuts is typically on the order of twenty millimeters. The insert is inserted between the installed femoral implant and the tibial implant. In a full knee implant the insert has two bearing surfaces that are shaped to receive the condyle surfaces of the femoral implant.

In at least one exemplary embodiment, sensors 1106 can measure load and position. Sensors 1106 are placed in a charger 1116 prior to the implant surgery being performed. Charger 1116 provides a charge to an internal power source within sensors 1106 that will sustain sensor measurement and data transmission throughout the surgery. Charger 1116 can fully charge sensor 1106 or be used as a precautionary measure to insure the temporary power storage is holding sufficient charge. Charger 1116 can be charge via a wireless connection through a sterilized packaging. Sensors 1106 are in communication with processing unit 1122. Sensors 1106 include a transmitter for sending data. Processing unit 1122 can be logic circuitry, a digital signal processor, microcontroller, microprocessor, or part of a system having computing capability. As shown, processing unit 1122 is a notebook computer having a display 1124. The communication between sensors 1106 and processing unit 1122 can be wired or wireless. In one embodiment, receiver 1118 is coupled to processing for wireless communication. A carrier signal for data transmitted from sensors 1106 can be radio frequency, infrared, optical, acoustic, and microwave to name but a few. In a non-limiting example, receiver 1118 receives data via a radio frequency signal in a short range unlicensed band sufficient for transmission within the size of an operating room. Information from processing unit 1122 can be sent through the internet to dynamic data repository and registry 1134 for long-term storage. The dynamic data repository and registry 1134 will be discussed in greater detail hereinbelow. In one embodiment, the data is stored in a server 1136 or as part of a larger database.

The surgeon uses system 1100 to aid in the preparation of bone surfaces, to measure loading, to measure balance, check alignment, and tune the knee joint prior to a final insert being installed. A reader 1120 is used to scan in information prior to or during the surgery. In one embodiment, the reader 1120 can be wired or wirelessly coupled to the processing unit 1122. Processing unit 1122 can process the information, display it on display 1124 for use during a procedure, and store it in memory or a database for long-term use. For example, information on components used in the surgery such as the artificial knee components or components of system 1100 can be converted to an electronic digital form using reader 1120 during the procedure. Similarly, patient information or procedural information can also be scanned in, input manually, or captured by other means to processing unit 1122.

The leg is placed in extension and the knee joint is exposed by incision. In one embodiment, the surgeon prepares the proximal end of the tibia. The prepared tibial surface is typically at a 90-degree angle to the mechanical axis of the leg. Targets 1110 are placed overlying the mechanical axis near the ankle and hip joint. The surgeon can select one of the spacer blocks 1102 or dynamic distractor 1104 for insertion in the joint region. The selected spacer block has a predetermined thickness that is imprinted on the spacer block or can be displayed on display 1124 by scanning the information. Alternatively, distractor 1104 is distracted by the surgeon within the joint region. The amount of distraction can be read off of distractor 1104 or can be displayed on display 1124.

In a non-limiting example of aligning two surfaces of the muscular-skeletal system, alignment of the leg to the mechanical axis is measured or a subjective check can be performed by the surgeon using an alignment aid. At least one component of the alignment aid is disposable. The alignment aid comprises lasers 1114 in the handle 1112 of the selected spacer block or a handle 1132 of distractor 1104 with the leg in extension. The alignment aid further includes targets 1110. Targets 1110, lasers 1114, or both can be disposable. Accelerometers in sensors 1106 provide positional information of the tibia in relation to the femur. For example, display 1124 will indicate that the angle between the tibia and femur is 180 degrees when the leg is in extension. The beam from lasers 1114 hit targets 1110 and provides a measurement of the position of the tibia in relation to the femur compared to the mechanical axis of the leg. In one embodiment, lasers 1114 are centrally located above the knee joint overlying the mechanical axis of the leg. The beam from lasers 1114 is directed perpendicular to the plane of the surface of the tibia. The beam from lasers 1114 will align and overlie the mechanical axis if the surface of the tibia is the perpendicular to the mechanical axis. The beam from lasers 1114 would hit targets 1110 at a point that indicates alignment with the mechanical axis. A valgus or vargus reading can be read where the beam hits the calibrated markings of targets 1110 if the leg is not aligned. The surgeon can then make an adjustment to bring the leg into closer alignment to the mechanical axis if deemed necessary. Jigs or cutting blocks can also be used in conjunction with lasers 1114 and targets 1110 to check alignment prior to shaping. The jigs or cutting blocks are used to shape the bone for receiving an implant. The distal end of femur and the proximal end of tibia are shaped for receiving orthopedic joint implants. In a further embodiment, sensors can be attached to the cutting jigs or devices to aid the surgeon in optimizing the depth and angles of their cuts.

Sensors 1106 measure the loading in each compartment for the depth or thickness of the selected spacer block or the distracted gap generated by distractor 1104. In one embodiment, the loading measurements are taken after the initial bone cuts are determined to be within a predetermined range of alignment with the mechanical axis. The load measurement in each compartment is either high, within an acceptable predetermined range, or low. A load measurement above a predetermined range can be adjusted by removing bone material, selecting a thinner spacer block, adjusting the gap of distractor 1104, or by soft tissue release. In general, the gap between the femur and tibia at which the measurement taken corresponds to a final insert thickness. In one embodiment, the gap is selected to result in a load measurement on the high side of the predetermined range to allow for fine-tuning through soft tissue release. Conversely, a load measurement below the predetermined range can be increased using the next thicker spacer block or by increasing the gap of distractor 1104. Data from sensors 1106 is transmitted to processing unit 1122. Processing unit 1122 processes the data and displays the information on display 1124 for use by the surgeon to aid in fine-tuning. Display 1124 would further provide positional information of the femur and tibia. The absolute loading in each compartment is measured and displayed on display 1124. As is known by one skilled in the art, the gap created by the bone cuts accommodates the combined thickness of the femoral implant, the tibial implant, and the insert. The gap using spacer blocks 1102 or distractor 1104 takes into account the combined thickness of the implant components. In a non-limiting example, the gap is chosen based on the availability of different thicknesses of the final insert. Thus, the loading on the final or permanent insert placed in the joint will measure within the predetermined range as prepared by using system 1100.

Balance is a comparison of the load measurement of each condyle surface. In general, balance correction is performed when the measurements exceed a predetermined difference value. Soft tissue balancing is achieved by loosening ligaments on the side of the compartment that measures a higher loading. In one embodiment, system 1100 allows the surgeon to read the loading measurement for each compartment on one or more displays on spacer blocks 1102 or distractor 1104. Another factor is that the difference in loading can be due to surface preparation of the bony cuts for either femoral implant or the tibial implant. If the differential is substantial, the surgeon has the option of removing bone on either surface underlying the implant to reduce the loading difference.

In one embodiment, the absolute load adjustments and balance adjustments are performed by soft tissue release in response to the assessment of each compartment. Load and balance adjustment is achieved with the selected spacer block or distractor 1104 in the knee joint. Spacer blocks 1102 and distractor 1104 have a gap to provide peripheral access between the superior and inferior surfaces of the device thereby giving the surgeon access to perform soft tissue release to either compartment with real time load measurement shown on display 1124. In at least one exemplary embodiment, handles 1112 of spacer blocks 1102 or handle 1132 of distractor 1104 can be removed or positioned. Handles 1112 or handle 1132 can be positioned away from the surgical area or removed allowing the surgeon access to perform soft tissue release. The soft tissue release is performed to each compartment to adjust the absolute loading within the predetermined range and further adjustment can be performed to reduce the differential loading between the compartments to within a predetermined differential range. Consequently, the surgical outcome is a function of system 1100 as complemented with the surgeon's abilities but not so highly dependent alone on the surgeon's skill. The device captures the "feel" of how an implanted device should properly operate to improve precision and minimize variation including haptic and visual cues.

A similar process is applied with the lower leg in flexion with tibia forming a 90-degree angle with the femur. In one embodiment, one or more bone cuts are made to the distal end of femur for receiving the femoral implant. The preparation of the femur corresponds to the leg in extension. As disclosed above, the selected spacer block or distractor 1104 can be coupled using an uprod from handle 1112 or handle 1132 to cutting block 1130 to aid in alignment and stability. In particular, the surface of the distal end of femur is cut parallel to the prepared surface of the tibia with the leg in flexion. The bone cut to the femur yields an imaginary rectangle formed with the parallel surfaces of femur and tibia when the leg is in extension. It should be noted that a portion of the femoral condyle is in contact with the selected spacer block or distractor 1104 with the leg in flexion and this region is not prepared at this time. In a subsequent step, the remaining surface of the distal end of the femur is prepared. The width of the gap in extension and in flexion between the cut distal end of the femur and the prepared tibia surface corresponds to the thickness of the combined orthopedic implant device comprising the femoral implant, final insert, the tibial implant. Ideally, the measured the gap under equal loading in flexion (e.g. the tibia forms a 90 degree angle with the femur) and extension is similar or equal. The prepared femoral surfaces and the prepared tibial surfaces are parallel throughout the range of motion and perpendicular to the mechanical axis of the leg.

Load measurements are made with the leg in flexion and the selected spacer block or distractor 1104 between the distal end of the femur and the tibial surface. In a non-limiting example, the measurements as described above should be similar to the measurements made in extension. Adjustments to the load value and the balance between compartments can be made by soft tissue release, or femoral component rotation in flexion with the selected spacer block or distractor 1104 in place. Alternatively, the femoral implant can be seated on the distal end of the femur and measurements taken. Adjustments can be made with the femoral implant in place. Furthermore, a gap generated by distractor 1104 can be adjusted to accommodate differences due to the femoral implant if required.

The leg with the selected spacer block or distractor 1104 can be taken through a complete range of motion. The loading in each compartment can be monitored on display 1124 and processed by processing unit 1122 over the range of motion. Processing unit can compare different points in the range of motion to the predetermined load range and the predetermined differential load range. Should an out of range/value condition occur, the surgeon can view and note the position of the femur and tibia position on display 1124 and take steps to bring the implant within specification. The surgeon can complete the implant surgery having knowledge that both qualitative and quantitative information was used during the procedure to ensure correct installation. In one embodiment, sensors 1106, disposable targets 1110, and lasers 1114 are disposed of upon completion of the surgery.

For example, the sensors will enable the surgeon to measure joint loading while utilizing soft tissue tensioning to adjust balance and maximize stability of an implanted joint. Similarly, measured data in conjunction with positioning can be collected before and during surgery to aid the surgeon in ensuring that, the implanted device has an equivalent geometry and range of motion.

Figure 12:
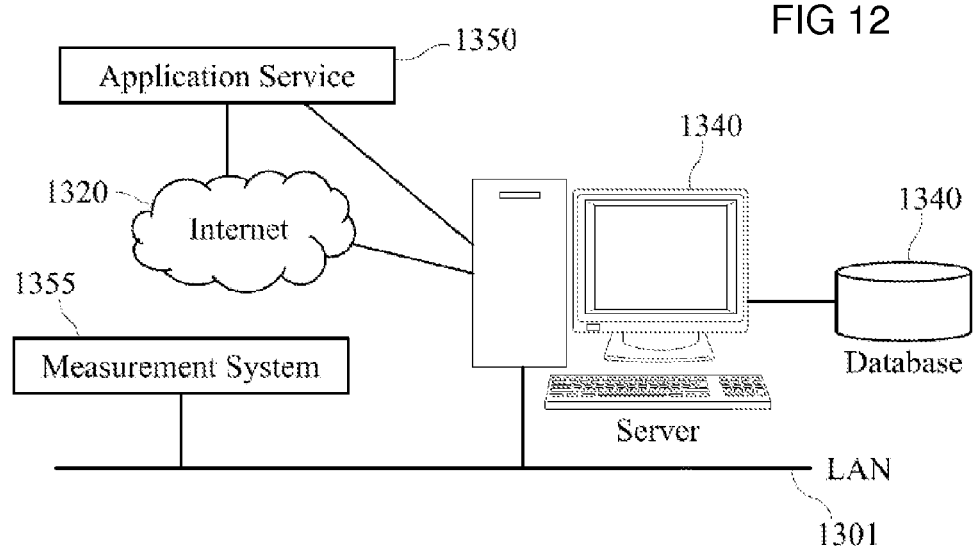
FIG. 12 depicts an exemplary diagrammatic representation of a machine in the form of a computer system within which a set of instructions, when executed, may cause the machine to perform any one or more of the methodologies discussed above.

Element 1340 of FIG. 12 depicts an exemplary diagrammatic representation of a machine in the form of a computer system within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system may include a processor (e.g., a central processing unit (CPU), a graphics processing unit (GPU, or both), a main memory and a static memory, which communicate with each other via a bus. The computer system may further include a video display unit (e.g., a liquid crystal display (LCD), a flat panel, a solid-state display, or a cathode ray tube (CRT)). The computer system may include an input device (e.g., a keyboard), a cursor control device (e.g., a mouse), a disk drive unit, a signal generation device (e.g., a speaker or remote control) and a network interface device.

The disk drive unit may include a machine-readable medium on which is stored one or more sets of instructions (e.g., software) embodying any one or more of the methodologies or functions described herein, including those methods illustrated above. The instructions may also reside, completely or at least partially, within the main memory, the static memory, and/or within the processor during execution thereof by the computer system. The main memory and the processor also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions, or that which receives and executes instructions from a propagated signal so that a device connected to a network environment can send or receive voice, video or data, and to communicate over the network using the instructions. The instructions may further be transmitted or received over a network via the network interface device.

While the machine-readable medium is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Figure 13:
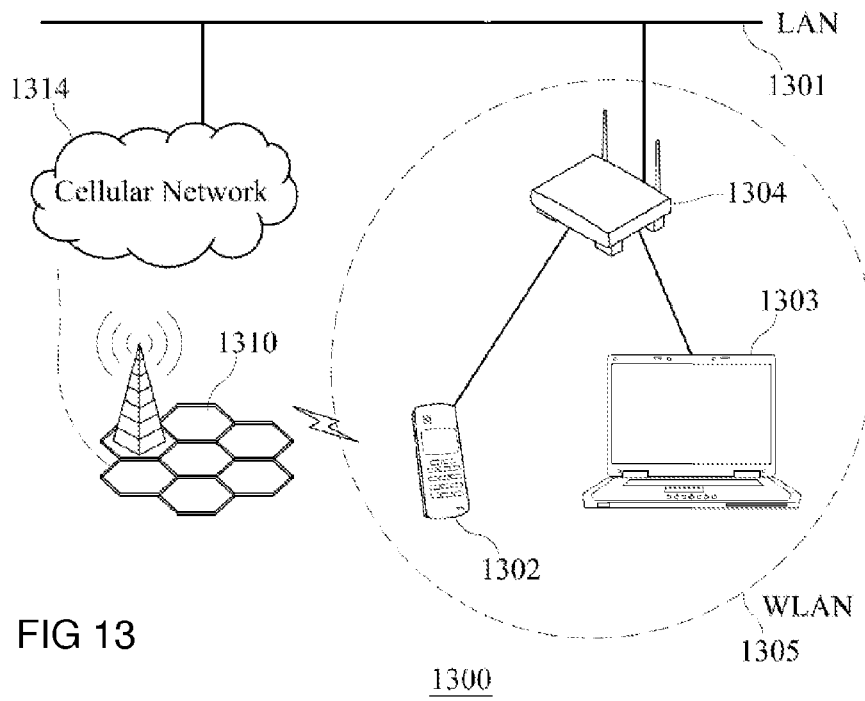
FIG. 13 is an illustration of a communication network for measurement and reporting in accordance with an exemplary embodiment.

FIG. 12 and FIG. 13 illustrate a communication network 1300 for measurement and reporting in accordance with an exemplary embodiment. Briefly, the communication network 1300 expands broad data connectivity to other devices or services. As illustrated, the measurement and reporting system 1300 can be communicatively coupled to the communications network 1300 and any associated systems or services.

As one example, the measurement system 1355 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 1300 can further be tied to an Electronic Medical Records (EMR) system to implement health information technology practices. In other embodiments, the communication network 1300 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 1300 can provide wired or wireless connectivity over a Local Area Network (LAN) 1301, a Wireless Local Area Network (WLAN) 1305, a Cellular Network 1314, and/or other radio frequency (RF) system (see FIG. 4). The LAN 1301 and WLAN 1305 can be communicatively coupled to the Internet 1320, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 1300 can utilize common computing and communications technologies to support circuit-switched and/or packet-switched communications. Each of the standards for Internet 1320 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 1314 can support voice and data services over a number of access technologies such as GSM-GPRS, EDGE, CDMA, UMTS, WiMAX, 2G, 3G, WAP, software defined radio (SDR), and other known technologies. The cellular network 1314 can be coupled to base receiver 1310 under a frequency-reuse plan for communicating with mobile devices 1302.

The base receiver 1310, in turn, can connect the mobile device 1302 to the Internet 1320 over a packet switched link. The internet 1320 can support application services and service layers for distributing data from the measurement system 1355 to the mobile device 1302. The mobile device 1302 can also connect to other communication devices through the Internet 1320 using a wireless communication channel.

The mobile device 1302 can also connect to the Internet 1320 over the WLAN 1305. Wireless Local Access Networks (WLANs) provide wireless access within a local geographical area. WLANs are typically composed of a cluster of Access Points (APs) 1304 also known as base stations. The measurement system 1355 can communicate with other WLAN stations such as laptop 1303 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etc).

By way of the communication network 1300, the measurement system 1355 can establish connections with a remote server 1330 on the network and with other mobile devices for exchanging data. The remote server 1330 can have access to a database 1340 that is stored locally or remotely and which can contain application specific data. The remote server 1330 can also host application services directly, or over the internet 1320.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

Figure 14:
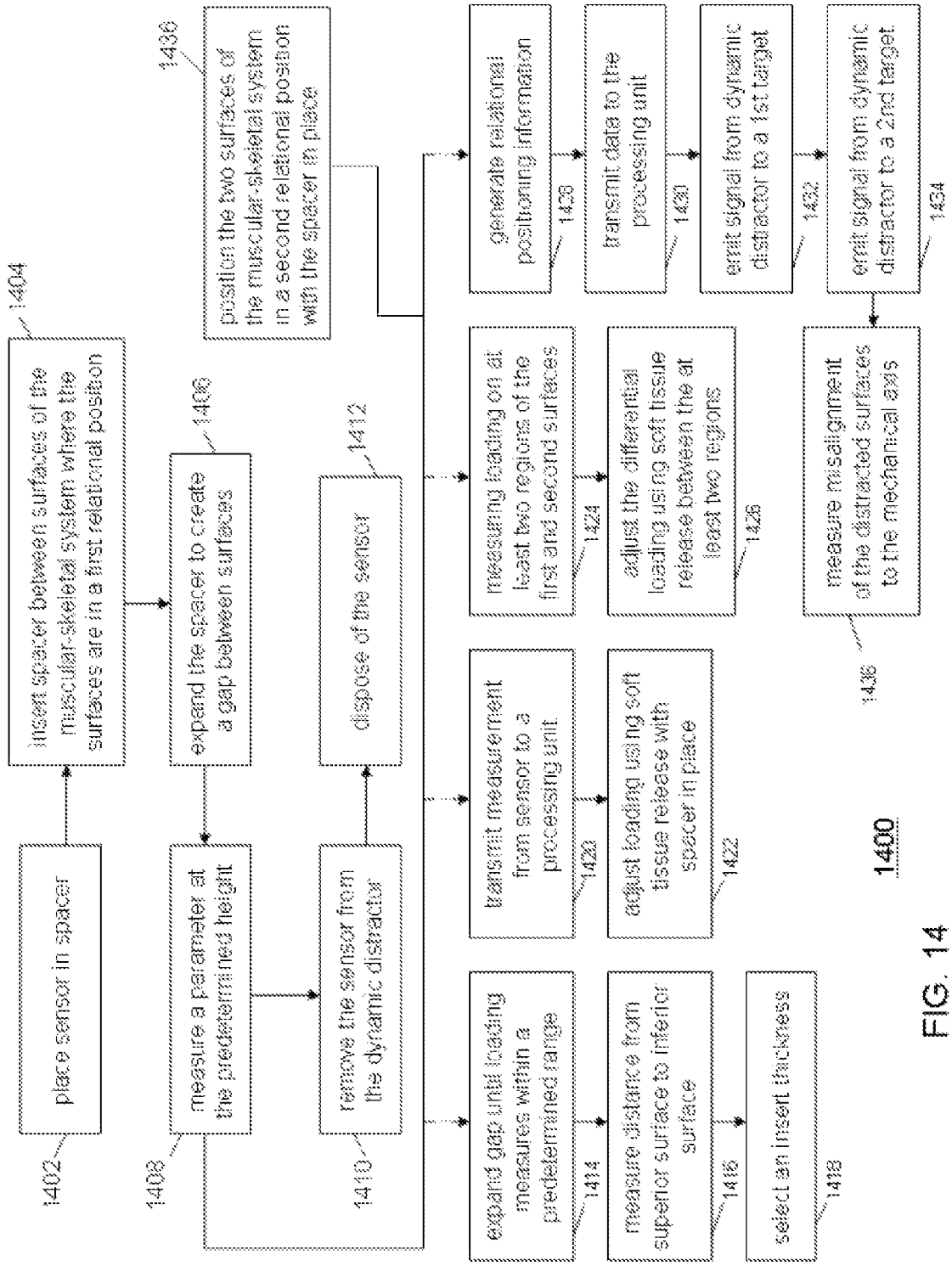
FIG. 14 is an exemplary method for distracting surfaces of the muscular-skeletal system in accordance with an exemplary embodiment.

FIG. 14 is an exemplary method 1400 for distracting surfaces of the muscular-skeletal system in accordance with an exemplary embodiment. The method can be practiced with more or less than the number of steps shown and is not limited to the order shown. In general, a spacer can have a fixed height or can be variable. The spacer is placed between surfaces of the muscular-skeletal system to distract or separate the surfaces. The spacer can include a handle to direct the spacer into the muscular-skeletal system. In one embodiment, the spacer is used to separate a joint region. A spacer with a fixed height is also known as a spacer block. A spacer having variable height is known as a distractor. In one embodiment, a distractor includes a lift mechanism as disclosed herein that can precisely adjust a height between surfaces to create a gap in the muscular-skeletal system of a predetermined value. A dynamic distractor includes one or more sensors that can measure a parameter of the muscular-skeletal system in real time. A variable height spacer can comprise a predetermined height in one state and a compressible height in a second state. The second state allows compression of the spacer as the muscular-skeletal system is moved from a first relational position to a second relational position. The variable height spacer can then be fixed to the predetermined height once positioned in the second relational position.

In a step 1402, sterilized sensors are removed from packaging. The sensors are powered up and enabled for sensing. One or more sensors coupled to a sensor for measuring a parameter of the muscular-skeletal system. For example, sensors are placed overlying a superior surface of a dynamic distractor. In the example, the sensors are used to measure load and balance for a knee reconstruction procedure. In one embodiment, the sensors are placed in a cavity on the superior surface of the distractor. Each sensor corresponds to a compartment of the knee. The dynamic distractor is also in a sterilized condition.

In a step 1404, the spacer is inserted in the muscular-skeletal system. The surfaces of the spacer are in contact with surfaces of muscular-skeletal system to be distracted. The surfaces of the muscular-skeletal system are in a first relational position. Continuing with the knee example, the inferior surface of the dynamic distractor is coupled to the proximal end of the tibia and the superior surface is coupled to the distal end of the femur. In one embodiment, the distal end of the tibia is prepared having a flat surface that is perpendicular to the mechanical axis of the leg.

In a step 1406, a dynamic distractor is used to vary a gap between the surfaces of the muscular skeletal system. In the knee example, a handle coupled to a lift mechanism of the dynamic distractor rotated to increase a gap between the inferior and superior surfaces. As the gap increases the inferior surface is in contact with the distal end of the tibia. Similarly, the superior surface of the dynamic distractor contacts the distal end of the femur. In one embodiment, the condyles of the distal end of the femur or the condyles of a femoral implant contact the corresponding sensors in each compartment of the dynamic distractor. The dynamic distractor is placed in the knee joint such that the dynamic distractor is centrally located in the knee joint. In one embodiment, the mechanical axis of the leg aligns to a feature of the dynamic distractor between the medial and lateral sides of the device. The handle of the dynamic distractor extends away from the knee joint on the mechanical axis of the leg.

In a step 1408, a parameter is measured by the sensors. The parameter is a quantitative measurement such as distance, weight, strain, force, load, pressure, wear, vibration, viscosity, and density that relate and characterize the procedure being performed. For illustration purposes the sensors measure load, pressure, or force. In the knee example, the loading in each compartment of the knee is measured at the height or gap created by the dynamic distractor. Similarly, the parameter measurement can be taken using the sensors overlying a spacer of a predetermined height. In one embodiment, the gap or height of distraction relates to the thickness of one or more components of an artificial joint such as the knee joint. The gap can correspond to the thickness of a final insert of the artificial joint. In general, final inserts typically comprise a polymer that provide a low-friction low-wear bearing surface. The final inserts are typically provided in a number of predetermined thicknesses of which one is selected for permanent insertion.

In a step 1410, the one or more sensors are removed from the spacer. In general, the sensor is removed after all quantitative measurements have been taken during the procedure. In a step 1412, the sensor is disposed of after the procedure is completed. For example, the sensors can be exposed to biological waste and require disposal as a biological hazard. The sensors as a disposable item alleviate substantial problems facing the health care industry. The high capital cost of traditional of surgical equipment often prevent purchase thereby preventing potentially beneficial equipment from being used. Disposables also eliminate the costly and time-consuming process of sterilization. The low cost of the sensors eliminates the capital cost issue thereby opening quantitative measurement of joint implants to a much larger audience. The result will be more consistent surgeries, ability to fine tune the surgery, longer implant life, and reduced post surgical complications to name but a few.

In general, a modification to the muscular-skeletal, a quantitative measurement, or both is performed with the surfaces of the muscular-skeletal in more than one relational position. In one embodiment, the surfaces of the muscular-skeletal system are positioned in a first relational position. A modification to the muscular-skeletal system is performed. The modification can affect the parameter being measured. In a step 1436, the two surfaces are positioned in a second relational position. In one embodiment, the spacer is not removed during the process of repositioning the surfaces of the muscular-skeletal system. A modification to the muscular-skeletal system, a quantitative measurement, or both can then be performed with the surfaces of the muscular-skeletal system in the second relational position.

Steps 1414, 1416, and 1418 illustrates an optimization process for a procedure with the dynamic distractor. In the knee example, steps 1414, 1416, and 1418 are an adjustment to optimize loading for a final insert of the artificial joint that maximizes the operating life of the device. The leg is placed in a first relational position. For example, the leg is placed in extension with the femur and tibia aligned with a mechanical axis of the leg. In general, it is not desirable for the implanted joint to be too tight or loose. In a step 1414, the gap is increased until the loading is within a predetermined loading range and the gap corresponds to an available final insert thickness. In one embodiment, the gap is selected for a final insert thickness that measures a loading above the median of the predetermined range to allow for soft tissue release back within the predetermined range. In a step 1416, the gap is measured when the sensors measure loading within the predetermined range. Alternatively, the dynamic distractor can increase or decrease gaps incrementally that correspond to available inserts. In a step 1418, the insert is selected. As mentioned previously, the measured gap when the loading is within the predetermined range may not correspond to a final insert thickness. The surgeon can increase or decrease the gap to an available insert thickness (and measure load in each compartment) then select an insert based on subsequent steps of the procedure to be implemented by the surgeon.

Steps 1420 and 1422 relate to adjustments made while a spacer is inserted. In one embodiment, the spacer is the dynamic distractor with one or more sensors. In a step 1420, data from the sensors is transmitted to a processing unit. In a non-limiting example, the processing unit is external to the dynamic distractor and sensors. As disclosed herein, the processing unit can be part of a notebook computer. The data from the sensors in the dynamic distractor can be displayed for viewing by the surgeon and medical team. In a step 1422, the surgeon can adjust the loading using soft tissue release techniques with the dynamic distractor in place. In one embodiment, the dynamic distractor can have a bellows or removable skirt around the periphery of the device that prevents debris from collecting within the interior. The bellows or removable skirt is removed to allow access along the medial and lateral periphery of the dynamic distractor and between the upper and lower support structures of the dynamic distractor. Further access for soft tissue release is provided by removing the handle of the dynamic distractor or positioning the handle away from the surgical area. Steps 1420 and 1422 can also be performed after the leg is moved into the second relational position. In the knee example, the leg is moved in flexion with the femur and tibia at less than a 180 degree angle. For example, the leg is moved in flexion at a 90 degree angle. Bone modification of the exposed distal end of the femur can also be preformed to prepare a bone surface for a femoral implant.

Steps 1424 and 1426 relate to adjustments made when parameters are measured in more than one region. In the knee example, measurements are made in the two knee compartments corresponding to the medial and lateral condyles (natural or artificial) in contact with the sensors. In a step 1424, the loading is measured in each compartment. In one embodiment, the measured loading in the two regions should be approximately equal. The differential loading can be measured and then adjusted if outside a predetermined differential load range. In general, the side measuring the higher loading is adjusted. In a step 1426, soft tissue release is performed to adjust the difference between the loadings measured in each compartment. As disclosed herein, the loading can be measured in real time as the release occurs. The loading is then adjusted until the difference between the compartments is within the predetermined differential load range thereby adjusting the joint towards the optimum based on measurement. Steps 1424 and 1426 can also be performed after the leg is moved into the second relational position. It should be noted that other adjustment methods can also be used in steps 1422 and 1426 if soft tissue release cannot produce the desired result. In some cases, the dynamic distractor is removed for complete access to the joint region allowing more substantial modification to occur.

Steps 1428, 1430, 1432, 1434, 1436, and 1438 relate to positioning and aligning the leg using the dynamic distractor. In step 1428, the leg is positioned using position information provided by the dynamic distractor. In one embodiment, accelerometers in the sensors provide information on the angle of the tibia in relation to the femur. Thus, the leg can be put precisely in extension (e.g. a 180-degree angle between the femur and tibia) and in flexion (less than 180-degree angle, for example a 90 degree angle between the femur and tibia). In a step 430, the positional information can be sent to the processing unit and the information displayed on a display for viewing by the surgeon. The surgeon can place the leg in extension or flexion to prepare or shape the proximal end of the tibia or the distal end of the femur. In steps 1432 and 1434, the surgeon identifies the mechanical axis of the leg. In one embodiment, one or more lasers are coupled to the handle of the dynamic distractor in the knee joint. As mentioned previously, the handle of the dynamic distractor is located overlying the center of the knee. In the step 1432, a first laser emits a signal to a first target that is positioned proximally to the center of the ankle. The line from center of the ankle to the center of knee aligns with the mechanical axis of the leg. The first target is positioned where it overlies the mechanical axis on a plane corresponding to the beam from the first laser. Similarly, in a step 1434, a second laser emits a signal to a second target that is positioned proximally to the center of the femoral head. A straight line from the center of the femoral head through the center of the knee to the center of the ankle comprises the mechanical axis of the leg. The second target overlies the mechanical axis and is positioned on a plane corresponding to the beam from the second laser. The surgeon can then measure the misalignment of the leg to the mechanical axis and make corrections appropriately.

Figure 15:
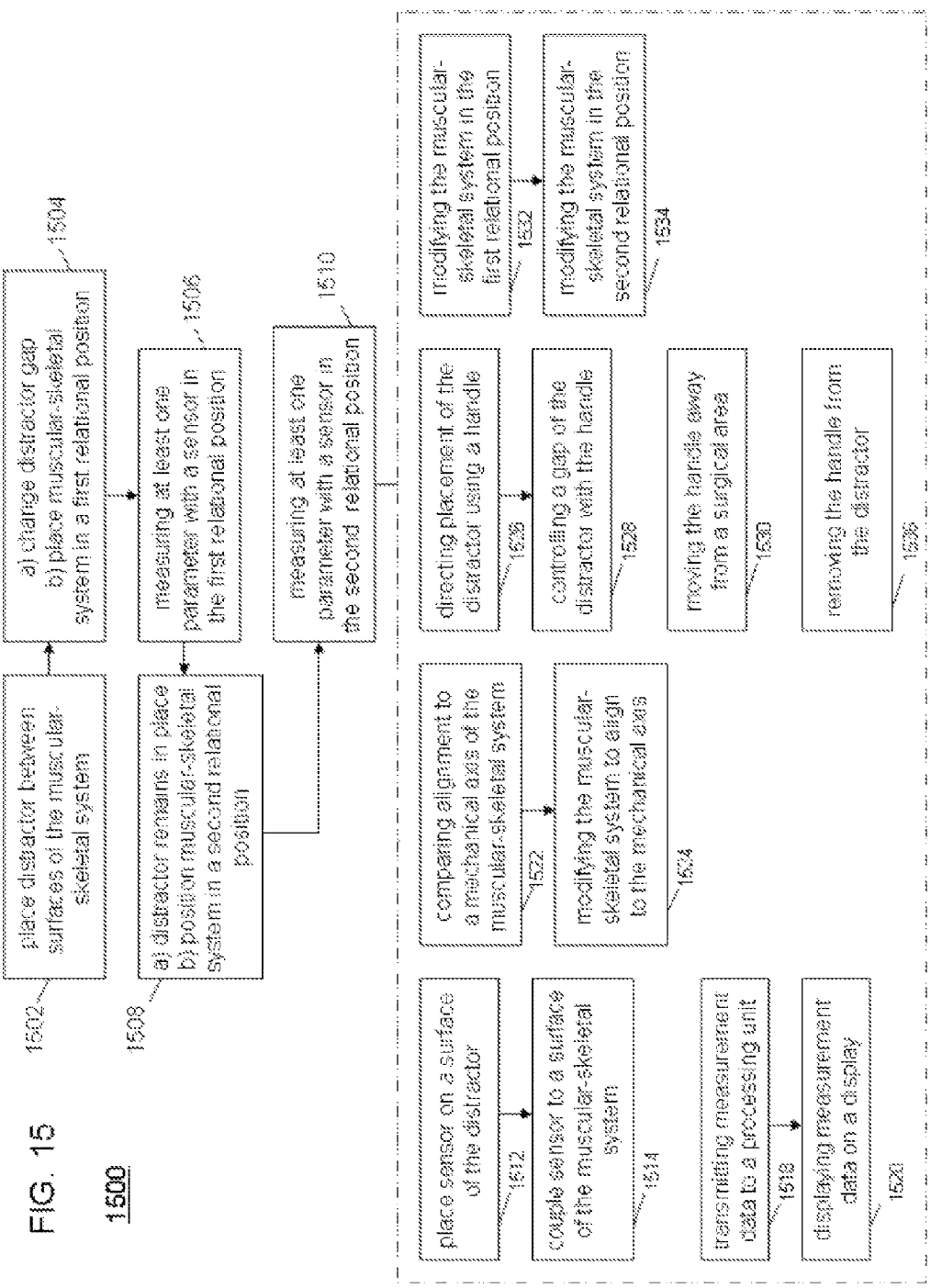
FIG. 15 is an exemplary method for distracting surfaces of the muscular-skeletal system in extension and in flexion in accordance with an exemplary embodiment.

FIG. 15 is an exemplary method 1500 for distracting surfaces of the muscular-skeletal system in extension and in flexion in accordance with an exemplary embodiment. The method can be practiced with more or less than the number of steps shown and is not limited to the order shown. In a step 1502, a distractor is placed between surfaces of a muscular-skeletal system. As mentioned previously, the distractor can be broadly used on the muscular-skeletal system including but not limited to the spinal column, knee, hip, ankle, shoulder, wrist, articulating, and non-articulating structures. As disclosed above, the distractor comprises a lift mechanism between a first support structure and a second support structure. In one embodiment, a handle couples to the lift mechanism to rotatably raise and lower the lift mechanism thereby changing a gap between the surfaces of the support structures. In general, the first and second supports structures are placed between two surfaces of the muscular-skeletal system. In a non-limiting example, to illustrate the principal, the distractor can be used in joint repair or replacement surgery to separate bones comprising the joint as they are prepared for an implant. Examples are vertebrae of the spinal column, the distal end of the femur and the proximal end of the tibia of a knee joint, or the pelvis and the proximal end of the femur of the hip.

In a step 1504, the gap provided by the distractor is changed and the muscular-skeletal system is placed in a first relational position. The gap of the distractor can be changed under the control of the surgeon thereby changing the spacing between the two surfaces of the muscular-skeletal system being distracted. In one embodiment, the gap corresponds to a thickness of one or more components to be implanted in the muscular-skeletal system. The distractor is likely to be initially placed between the two surfaces having a minimum gap and then expanded to a predetermined height or thickness. The muscular-skeletal system is placed in a first relational position with the distractor inserted between the two surfaces. The first relation position corresponds to the positions of the surfaces and portions of the muscular-skeletal system attached thereto.

In a step 1506, at least one parameter is measured with a sensor. The muscular-skeletal system is in the first relational position when parameter is measured by the sensor. In one embodiment, the distractor includes a sensor for measuring a parameter. For example, the sensor can provide accurate measurements of parameters such as distance, weight, strain, pressure, wear, vibration, viscosity, and density that relate to the procedure being performed. The distractor further provides two or more surfaces in contact with the muscular-skeletal system for close proximity measurement by the sensor. As disclosed hereinabove, the sensor can be self contained in a housing, can be placed in a cavity on one or more of the distracting surfaces and includes an exposed surface that can couple to the muscular-skeletal system for sensing.

In a step 1508, the muscular-skeletal system is repositioned to a second relational position. In a non-limiting example, the second relational position corresponds to movement of the distracted surfaces and portions of the muscular-skeletal system attached thereto in relation to one another. The position of the distracted surfaces in the second position is different from the position of the distracted surfaces in the first position. The distractor remains in place during positioning to the second relational position. This provides the benefit of reducing surgical time and stress on the patient. In general, the support structures of the distractor and more specifically the surfaces of the support structure allow natural movement of the muscular-skeletal in a normal range of motion.

In a step 1510, at least one parameter is measured by the sensor while in the second relational position. In one embodiment, the distractor remains in place while the measurement is taken. The surgeon or medical staff can compare measurement data with the muscular-skeletal system in two different positions. Often the measurement data will be similar throughout the range of motion or differ by a known amount due to geometrical differences of the position. Referring to a step 1518, the sensor can include a transmitter for transmitting measurement data from the sensor to a processing unit. The processing unit can be a logic circuit, digital signal processor, microcontroller, microprocessor, or analog circuitry. The processing unit can be part of a larger system such as a multi-component custom system or a commercially available notebook computer or personal computer. In a step 1520, the measurement is displayed on a display. The data can be processed by the processing unit and a GUI (graphical user interface) integrated with the display to present the data, enhance use of the data, interpret the data, and contemplate or detail corrections that may be needed to be made based on the data. The transmission of the data can occur as measurements over a range of motion and at least in the first relational position and the second relational position. In one embodiment, the distractor provides measurement data on the amount of distraction or gap produced by the device. This measurement data can also be transmitted along with the relational position data of the muscular-skeletal system. Thus, the distractor provides the benefit of measurement data being taken with the sensor at different points of the range of motion and at different gap heights without being removed.

In a step 1512, the sensor is placed on a surface of the distractor. In one embodiment, the sensor is a disposable device. The support structures of the distractor can have one or more recesses or cavities for receiving a sensor on a surface of the device. In particular, a cavity can be formed on a major surface of a support structure that comes in contact with a surface of the muscular-skeletal system during distraction. In a non-limiting example, one or more sensors are placed in one more cavities prior to insertion between the two surfaces of the muscular-skeletal system. The sensors are activated and in communication with the processing unit for taking measurements on the muscular-skeletal system. In a step 1514, the sensor is coupled to a surface of the muscular-skeletal system. As disclosed herein, the sensor can include a major surface that is exposed and substantially parallel to the major surface of a support structure. The sensor comes in contact with the muscular-skeletal system as the two surface of the muscular-skeletal system are distracted. Typically, as distraction increases a compressive force by the two surfaces of the muscular-skeletal system is applied to the two support structures placing the sensor in intimate contact with the surface. Alternatively, the sensor can be located on or in proximity to the distractor if direct contact is not required for the measurement.

In a step 1522, the alignment of at least one of the first or second relational position is compared to a mechanical axis of the muscular-skeletal system. Typically, the muscular-skeletal system has optimal alignments that maximize performance of the structure. The distractor can be used to measure misalignment to the mechanical axis. The distractor utilizes at least one of the surface being distracted to measure the misalignment. The distracted surface of the muscular-skeletal system has a geometric relationship with the mechanical axis. For example, the plane of the distracted surface can be a specific angle from the mechanical axis. Moreover, there can be specific landmarks of the surface that such as a center point that further identify the relationship with the mechanical axis.

In one embodiment, a plane of a portion of the surface of the distractor is co-planar with the muscular-skeletal surface it is contacting. This relationship is extended to a handle of the distractor where a surface of the handle is co-planar to the distracted surface of the muscular-skeletal system. The handle can also extend from muscular-skeletal system at a location corresponding to a landmark that corresponds to the mechanical axis. For example, it can extend centrally or at a specific position from the distracted surface. As disclosed hereinabove, a drop rod can be attached to an opening in the handle to visually and subjectively determine if alignment is within a predetermined range. The drop rod can also be coupled to other fixtures coupled to different areas of the muscular-skeletal system to measure alignment. Alternatively, one or more lasers can be attached to the handle of the distractor. The lasers are directed to one or more targets that are located along the mechanical axis. The amount of misalignment can be measured by the location where the beam hits a scale on each of the target.

In a step 1524, the muscular-skeletal system is modified to reduce the measured misalignment. In general, there will be an acceptable range for misalignment to the mechanical axis. Adjustments are made to reduce the error if the measurement is outside the acceptable range. Modifications to the muscular-skeletal system can take many forms. Material can be added or removed from the bone structure. Soft tissue release of the muscles, tendons, and ligaments can also be used to modify alignment. Additionally, other structures and materials that are both biological and artificial can be used to change or be added to the muscular-skeletal system to bring the two surfaces into alignment. After the modifications are performed, the alignment can be rechecked to verify that the misalignment error is with an acceptable range.

In a step 1526, the handle is used to direct the placement of the distractor between the two surfaces of the muscular-skeletal system. The handle of the distractor provides an external means for the surgeon to locate and position the first and second support structures of the distractor accurately in the muscular-skeletal system. In one embodiment, the handle is coupled to a lift mechanism that generates the gap between the first and second support structures. In a step 1528, the gap height can be varied using the handle. The handle is coupled to a shaft of the lift mechanism. In a non-limiting example, the handle is rotated to increase or decrease the gap of the distractor.

In a step 1530, the handle is moved away from the surgical area. The distractor is designed to provide access to areas in proximity to the two surfaces being distracted by the device. One access area is anterior to the two surfaces of the distracted muscular-skeletal system. Access is desirable to perform a surgical procedure or other step with the distractor in place. A benefit of the distractor is that the handle is hinged allowing it to be moved away from the area where the surgical procedure is being performed. Alternatively, in a step 1536, the handle is removed from the distractor also giving unobstructed anterior access. The distractor also has peripheral access and access between the first and second support structures when a gap is created. In one embodiment, the distractor has a bellows like skirt around the periphery of the device that is inserted between the two surfaces of the muscular-skeletal system. The skirt prevents materials or debris from the procedure from getting between the first and second support structures of the distractor. The skirt can be removed when a procedure is performed requiring anterior, posterior, medial, or lateral access. Alternatively, the periphery can be open and the interior space between the first and second support structures can be cleaned periodically to prevent build up of debris. The distractor provides open space anterior, posterior, medially, laterally, and between the first and second support structures allowing the surgeon great latitude in performing surgical procedures in proximity to the distracted area.

In a step 1532, the muscular-skeletal system is modified in the first relational position. As disclosed above, modifications to the muscular-skeletal system can take many forms. Bone modification, soft tissue release, implants, adding artificial or biological materials are but a few of the modifications that can be made using the access provided by the distractor. Similarly, in a step 1534, the muscular-skeletal system is modified in the second relational position. In one embodiment, the distractor is not removed during sensor measurement, movement through a range of motion, and during the modification process thereby greatly reducing the surgical time. Moreover, sensors in the distractor can provide real time measurement of how the modifications are affecting the distracted region. This instant feedback and quantitative measurement allow fine adjustments to be made that will greatly increase the consistency of orthopedic surgical procedures.

Figure 16:
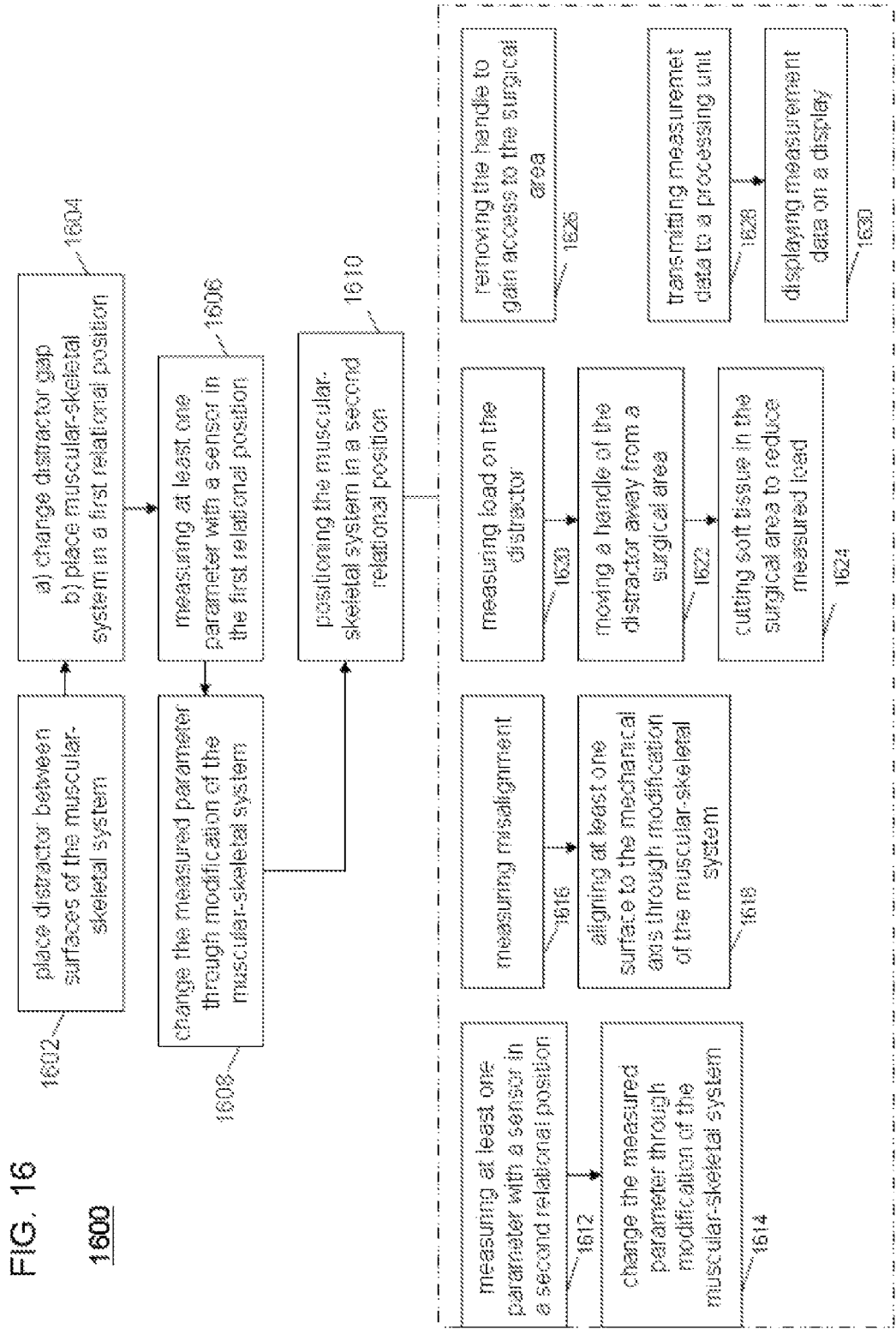
FIG. 16 is an exemplary method for distracting surfaces of the muscular-skeletal system in extension and in flexion in accordance with an exemplary embodiment.

FIG. 16 is an exemplary method 1600 for distracting surfaces of the muscular-skeletal system in extension and in flexion in accordance with an exemplary embodiment. The method can be practiced with more or less than the number of steps shown and is not limited to the order shown. Steps 1602, 1604, and 1606 are respectively similar to steps 1502, 1504, and 1506 of FIG. 15 and are not described here for brevity. In a step 1608, the measured parameter is changed through modification of the muscular-skeletal system. As mentioned previously, the distractor can be broadly used on the muscular-skeletal system including but not limited to the spinal column, knee, hip, ankle, shoulder, wrist, articulating, and non-articulating structures. In one embodiment, the measurement and the modification of the muscular-skeletal system occurs with the distractor in place and the leg in extension.

In a step 1610, the muscular-skeletal system is repositioned to a second relational position. As mentioned previously, the position of the distracted surfaces in the second position is different from the position of the distracted surfaces in the first position. The distractor remains in place during positioning to the second relational position. This provides the benefit of reducing surgical time and stress on the patient. In general, the support structures of the distractor and more specifically the surfaces of the support structure allow natural movement of the muscular-skeletal in a normal range of motion.

In a step 1612, at least one parameter is measured by the sensor while in the second relational position. In a step 1614, the measured parameter is changed through modification of the muscular-skeletal system. The modification occurs with the muscular-skeletal system in the second relational position. In one embodiment, the distractor remains in place while moving the muscular-skeletal system to the second relational position, during sensor measurement, and modification of the muscular-skeletal system. The surgeon or medical staff can compare measurement data with the muscular-skeletal system in at least two different positions. Referring to a step 1628, the sensor can include a transmitter for transmitting measurement data from the sensor to a processing unit. In a step 1630, the measurement is displayed on a display. For example, the processing unit can be the microprocessor of a notebook while the display is the screen of the notebook. The data is transmitted in real time when a measurement is taken. In other words, the data is transmitted, processed, and displayed during the measurement and subsequent modification of the muscular-skeletal system in the first relational position. Similarly, the data is transmitted, processed, and displayed during the measurement and subsequent modification in the second relational position. The transmission of measured data can sent wirelessly using a radio frequency signal.

In a step 1522, the alignment of at least one of the first or second relational position is compared to a mechanical axis of the muscular-skeletal system. Typically, the muscular-skeletal system has optimal alignments that maximize performance of the structure. The distractor can be used to measure misalignment to the mechanical axis. The distractor utilizes at least one of the surface being distracted to measure the misalignment. The distracted surface of the muscular-skeletal system has a geometric relationship with the mechanical axis. For example, the plane of the distracted surface can be a specific angle from the mechanical axis. Moreover, there can be specific landmarks of the surface that such as a center point that further identify the relationship with the mechanical axis.

In one embodiment, a plane of a portion of the surface of the distractor is co-planar with the muscular-skeletal surface it is contacting. This relationship is extended to a handle of the distractor where a surface of the handle is co-planar to the distracted surface of the muscular-skeletal system. The handle can also extend from muscular-skeletal system at a location corresponding to a landmark that corresponds to the mechanical axis. For example, it can extend centrally or at a specific position from the distracted surface. As disclosed hereinabove, a drop rod can be attached to an opening in the handle to visually and subjectively determine if alignment is within a predetermined range. The drop rod can also be coupled to other fixtures coupled to different areas of the muscular-skeletal system to measure alignment. Alternatively, one or more lasers can be attached to the handle of the distractor. The lasers are directed to one or more targets that are located along the mechanical axis. The amount of misalignment can be measured by the location where the beam hits a scale on each of the target.

In a step 1616, the misalignment of the muscular-skeletal system is measured. As disclosed above, the measurement can be made using lasers and targets respectively coupled to the handle of the distractor and located along the mechanical axis of the muscular-skeletal system. In one embodiment, the misalignment is referenced to at least one of the two surfaces being distracted by the distractor. The alignment of the surface of the muscular-skeletal system is compared to the mechanical axis. In a step 1618, the muscular-skeletal system is modified to reduce the measured misalignment. As mentioned previously, there is an acceptable range for misalignment to the mechanical axis. Adjustments are made to reduce the error if the measurement are outside the acceptable range. In one embodiment, the corrections can be checked in real time as the modifications are made to see that the changes to the muscular-skeletal system are moving the misalignment error to the acceptable range.

In a step 1620, the sensor measures load. In one embodiment, the two surfaces of the muscular-skeletal system place a compressive force across the first and second support structures of the distractor. One or more sensors on the first and second support structures of the distractor can be used to measure loading and the distribution of loading. In a step 1622, the handle of the distractor is moved away from a surgical area. In non-limiting example, the surgical area corresponds to a region where muscles, tendons, and ligaments couple the at least two surfaces of the muscular-skeletal system together. The handle is moved to a position such that modification to the soft tissue can take place. In a step 1624, soft tissue is cut in the surgical area to reduce loading applied by the two surfaces of the muscular-skeletal system on the distractor. In general, the sensor can measure load, pressure, or force. The distractor provides access for the surgeon to make cuts to the soft tissue with the area distracted. The sensor measures in real time allowing the surgeon to adjust the load to an optimal value. In a step 1626, the handle can be removed to further improve the anterior access.

Figure 17:
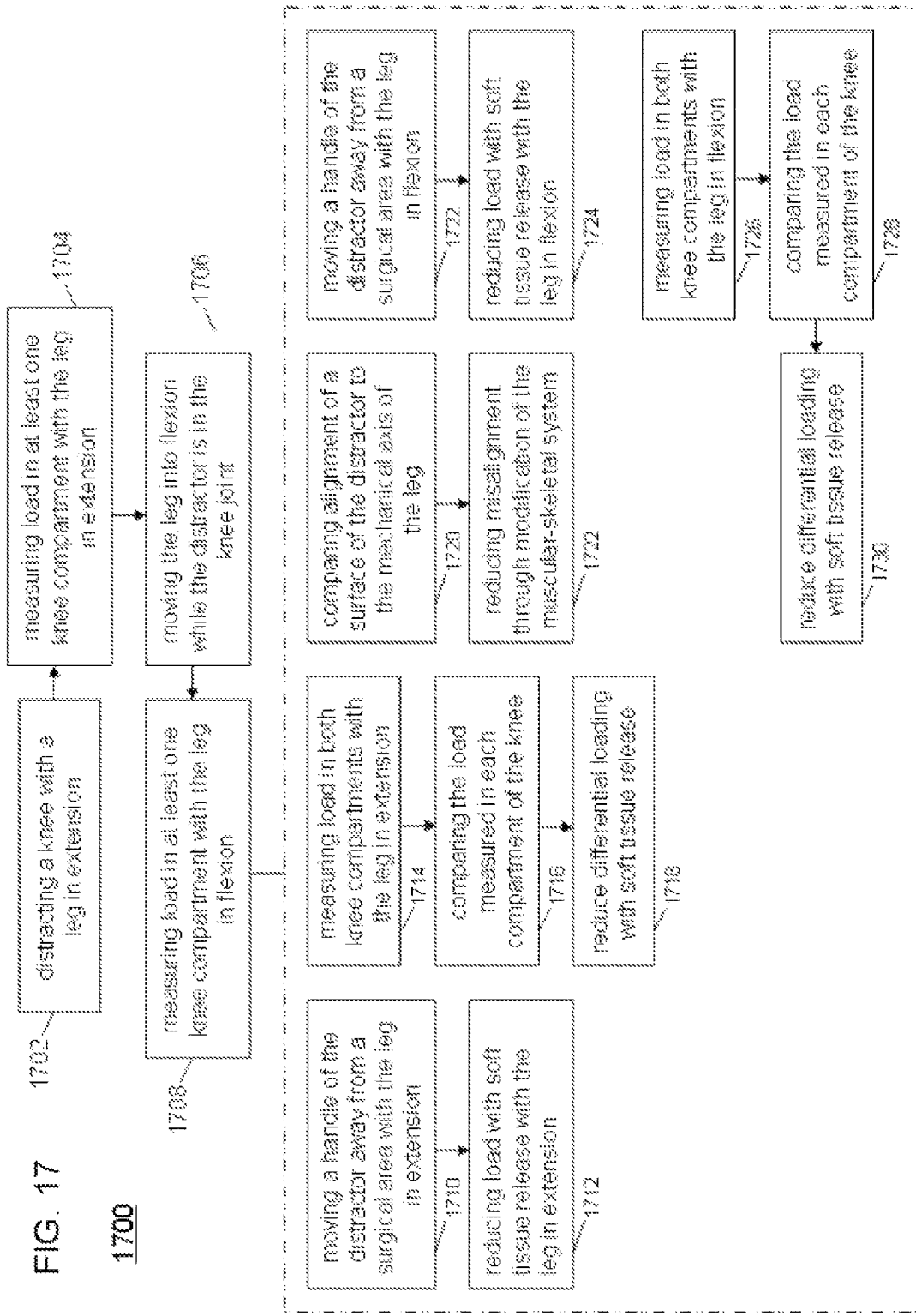
FIG. 17 is an exemplary method for distracting surfaces of a knee joint in extension and in flexion in accordance with an exemplary embodiment.

FIG. 17 is an exemplary method 1700 for distracting surfaces of a knee joint in extension and in flexion in accordance with an exemplary embodiment. The method can be practiced with more or less than the number of steps shown and is not limited to the order shown. A knee joint implant procedure of the muscular-skeletal system is used to illustrate the process of distraction. The knee joint comprises the distal end of the femur and the proximal end of the tibia. An artificial knee joint comprises a femoral implant, an insert, and a tibal implant. The femoral implant is shaped similar to and replaces the natural condyles at the distal end of the femur. The insert has a bearing surface for receiving the condyles and an inferior surface that mates and is retained by the tibial implant. In general, the artificial knee joint mimics the natural knee joint in operation once implanted.

All the steps for preparing a knee will not be disclosed for brevity but are well known by one skilled in the art. The knee is opened by incision to expose the distal end of the femur and the proximal end of the femur. The patella is removed or moved away from the knee joint region. The proximal end of the tibia is prepared by cutting the bone. In one embodiment, the proximal end of the tibia is prepared having a planar surface. In one embodiment, the planar surface is cut perpendicular to the mechanical axis of the leg. The distractor is then inserted into the knee joint.

The distractor has a first support structure having a superior surface for receiving the condyles of the femur and a second support structure having an inferior surface for mating to the prepared tibial surface. The shape of the support structures as disclosed herein allows natural movement of the leg through the range of motion with the distractor in place. In one embodiment, two sensors are placed in the superior surface of the distractor for measuring load in each compartment of the knee. A handle is used to direct the first and second support structures into the knee. The handle can be rotated to increase the gap of the distractor to place the superior surface of the first support structure in contact with the condyles of the femur and the inferior surface of the second support structure in contact to the tibial surface. More specifically, each condyle will contact a surface of a corresponding sensor.

In a step 1720, the alignment of a surface of the distractor is compared to the mechanical axis of the leg. The surface of the distractor corresponds to a surface of the knee. In one embodiment, the surface is the prepared surface of the tibia. Targets for leg alignment can be placed overlying the mechanical axis of the leg. Typically one target is placed in the ankle or foot region and a second target is placed in the hip joint region near the femoral head. The mechanical axis is a straight line from the center of the femoral head through the center of the knee joint to the center of the ankle. In one embodiment, handle extends from the knee joint at a point that corresponds to the center of the knee joint. The inferior surface of the second support structure is planar to the tibial surface. Similarly, one or more surfaces of the handle of the distractor is aligned to the inferior surface of the second support structure thereby being co-planar to the tibial surface. As disclosed hereinabove, lasers can be attached to the handle pointing towards the ankle target and the hip target. As mentioned previously, the tibial surface is prepared to be 90 degrees from the mechanical axis of the leg. Misalignment from the mechanical axis can be measured from where the beam of the laser hits the target. A correctly aligned leg will hit each target at a point representing the location of the mechanical axis. In a step 1722, the measured misalignment can be reduced through modification of the muscular-skeletal system. The modification can be to the bone, soft tissue, additional implants or materials (artificial and biological) that bring the femur and tibia into alignment with the mechanical axis.

In a step 1702, the knee joint is distracted with the leg in extension. The leg is in extension when the femur and tibia are positioned having a 180-degree angle between them. A handle of the distractor directs the support structures into the knee joint area. The handle is rotated to increase a gap between the superior and inferior surfaces until contact is respectively made to the condyles of the femur and the surface of the tibia. The sensors in each compartment of the first support structure are in communication with an external processing unit. In one embodiment, each condyle of the femur is in contact with a corresponding sensor surface throughout the range of motion of the leg. The surgeon positions the distractor such that the handle corresponds to the center of the knee joint, which aligns with the mechanical axis of the leg. In a non-limiting example, the leg alignment to the mechanical axis can be measured and corrections made to reduce misalignment if outside an acceptable range.

In a step 1704, a load is measured with the leg in extension for at least one compartment of the knee. The data is received by the processing unit and displayed on a display. For example, accelerometers in the sensors can show relative position of the femur to the tibia. In one embodiment, the femur and tibia are shown on the display to provide visual information to the surgeon on positioning. The angle between the femur and tibia can be displayed as well as alignment of the leg to the mechanical axis. The sensors include a measurement device such as a strain gauge to measure load. A complete knee replacement will measure loading on both compartments of the knee.

The distractor provides quantitative data that is used by the surgeon to prepare the knee. In a non-limiting example, the knee is distracted to a gap that corresponds to a combined insert and tibial implant thickness (the distal end of the femur is unprepared in the example). As is known by one skilled in the art, inserts are available in different sizes and thicknesses. The surgeon picks a size that is best adapted for the patient bone dimensions. The surgeon prepares the bone surfaces for an approximate combined thickness of the implants. For illustration purposes a combined implant thickness of 20 millimeters could be used. Typically, several insert thicknesses are suitable based on the tibial cut and the resulting gap between the tibial surface and the condyles of the femur. The sensor measurements are used to select an appropriate range and allows fine-tuning of the loading to within a very accurate range. For the full joint replacement, the gap height of the distractor, angle between tibia/femur (180 degrees, leg in extension), the loading on each compartment at the gap height, and the differential loading between the compartments is transmitted and displayed for viewing by the surgeon.

In a non-limiting example, the surgeon may have to increase or decrease the gap height of the distractor depending on the sensor readings. The increase or decrease in gap height will correspond to an available insert thickness. In one embodiment, the surgeon adjusts the gap height to measure load on the high side of a predetermined load range for each compartment. Selecting on a high side reading allows for fine adjustments to the final load value in a subsequent step. In general, the surgeon selects the appropriate insert size for the knee implant.

In a step 1706, the leg is moved into flexion while the distractor remains in the knee joint. As mentioned previously, the distractor provides surfaces that allows movement of the joint through the natural range of motion. This provides the benefit of being able to prepare the leg for load, balance, and alignment in more than one position using a single device. In one embodiment, the gap height of the distractor remains in the selected height for the leg in extension. Alternatively, the gap height of the distractor can be reduced while moving the leg in flexion to a final position and then readjusting the gap. In a non-limiting example, the leg is moved in flexion to a position where the femur and tibia form a 90-degree angle. In one embodiment, the surgeon can move the leg while viewing femur/tibia angle on the screen to get it precisely positioned.

In a step 1708, the load in at least one knee compartment is measured with the leg in flexion. In a non-limiting example, the gap height of the distractor in flexion is equal to the gap height selected by the surgeon when the leg was in extension. The sensors communicate with the processing unit providing the measured load in each compartment, differential loading between compartments, and the gap height to the surgeon with the leg in flexion. Thus, the leg can be moved from extension to flexion with the distractor in place. The sensors can measure load and differential loading in different positions and gap heights that can be displayed on a screen for the surgeon to view. The data is also stored in memory for use.

In a step 1710, the handle of the distractor is moved from a surgical area with the leg in extension. As mentioned previously, the handle of the distractor includes a hinge to position the handle away from a surgical area or can be removed to have anterior access to the distracted area. The surgical area corresponds to the muscle and ligaments coupling the femur to the tibia. The muscle and ligaments in the surgical area are located laterally and medially around the knee joint. A space is typically opened between the first and second support structures when the knee joint is distracted. Thus, the distractor enables soft tissue release by providing access from multiple vantage points to the muscle and ligaments with the device in place.

In a step 1712, the load in at least one compartment of the knee is reduced with the leg in extension. The handle is positioned to allow anterior and peripheral access to the soft tissue for incision. The surgeon can also place a scalpel between the first and second support structures for an interior or peripheral cut to the soft tissue if needed. In a non-limiting example, the soft tissue release can be performed when the leg is in extension after the loading is measured and the gap adjusted to a height selected by the surgeon. The soft tissue release can be performed on either the lateral or the medial sides of the knee or on both sides. In one embodiment, the soft tissue release is performed to bring each compartment loading within a predetermine loading range. The sensor data is transmitted, processed, and displayed in real time allowing the surgeon to view the actual measured effect of each cut on the loading in both compartments.

Referring to a step 1714, the load, force, or pressure in both knee compartments are measured with the leg in extension. In a step 1716, the measured load in each compartment is compared and a differential loading is calculated. In a step 1718, the differential loading between the two knee compartments is reduced using soft tissue release with the distractor in the knee joint. The surgeon can fine-tune the leg in extension to balance the loading between compartments with the distractor in place. In one embodiment, the surgeon can reduce the measured load on the side reading the highest value and bring the differential loading down within a predetermined differential loading range. In the example, the absolute loading measured in each compartment has also been reduced within a predetermined acceptable load range. As previously disclosed, the gap generated by the distractor corresponds to an available thickness insert of the artificial knee joint. The display can provide indicators to the surgeon when the measured load or the differential load is within their respective appropriate ranges.

In a step 1722, the handle of the distractor is moved from a surgical area with the leg in flexion. As mentioned previously, the leg is positioned with the femur and tibia at a right angle. In a step 1724, the load in at least one compartment of the knee is reduced with the leg in flexion. The handle is positioned to allow anterior and peripheral access to the soft tissue for incision. The surgeon can also place a scalpel between the first and second support structures for an interior or peripheral cut to the soft tissue if needed. In a non-limiting example, the soft tissue release can be performed when the leg is in extension after the loading is measured and the gap adjusted to a height selected by the surgeon. The soft tissue release can be performed on either the lateral or the medial sides of the knee or on both sides. In one embodiment, the soft tissue release is performed to bring each compartment loading within a predetermine loading range. The sensor data is transmitted, processed, and displayed in real time allowing the surgeon to view the actual measured effect of each cut on the loading in both compartments with the leg in flexion.

In a step 1726, the load, force, or pressure in both knee compartments are measured with the leg in flexion. In a step 1728, the measured load in each compartment is compared and a differential loading is calculated. In a step 1730, the differential loading between the two knee compartments with the leg in flexion is reduced using soft tissue release with the distractor in the knee joint. The surgeon can fine-tune the leg in extension to balance the loading between compartments with the distractor in place. In one embodiment, the surgeon can reduce the measured load on the side reading the highest value and bring the differential loading down within a predetermined differential loading range. In the example, the absolute loading measured in each compartment has also been reduced within a predetermined acceptable load range. As previously disclosed, the gap generated by the distractor corresponds to an available thickness insert of the artificial knee joint. In the non-limiting example, the gap created by the distractor in extension and flexion is the same. The display can provide indicators to the surgeon when the measured load or the differential load is within their respective appropriate ranges when the leg is in flexion. The surgeon can take further measurements on load and balance by moving the leg in different positions of flexion and recording the values. Further adjustments could be made to refine load and balance in these other flexion positions with the distractor in place.

Figure 18:
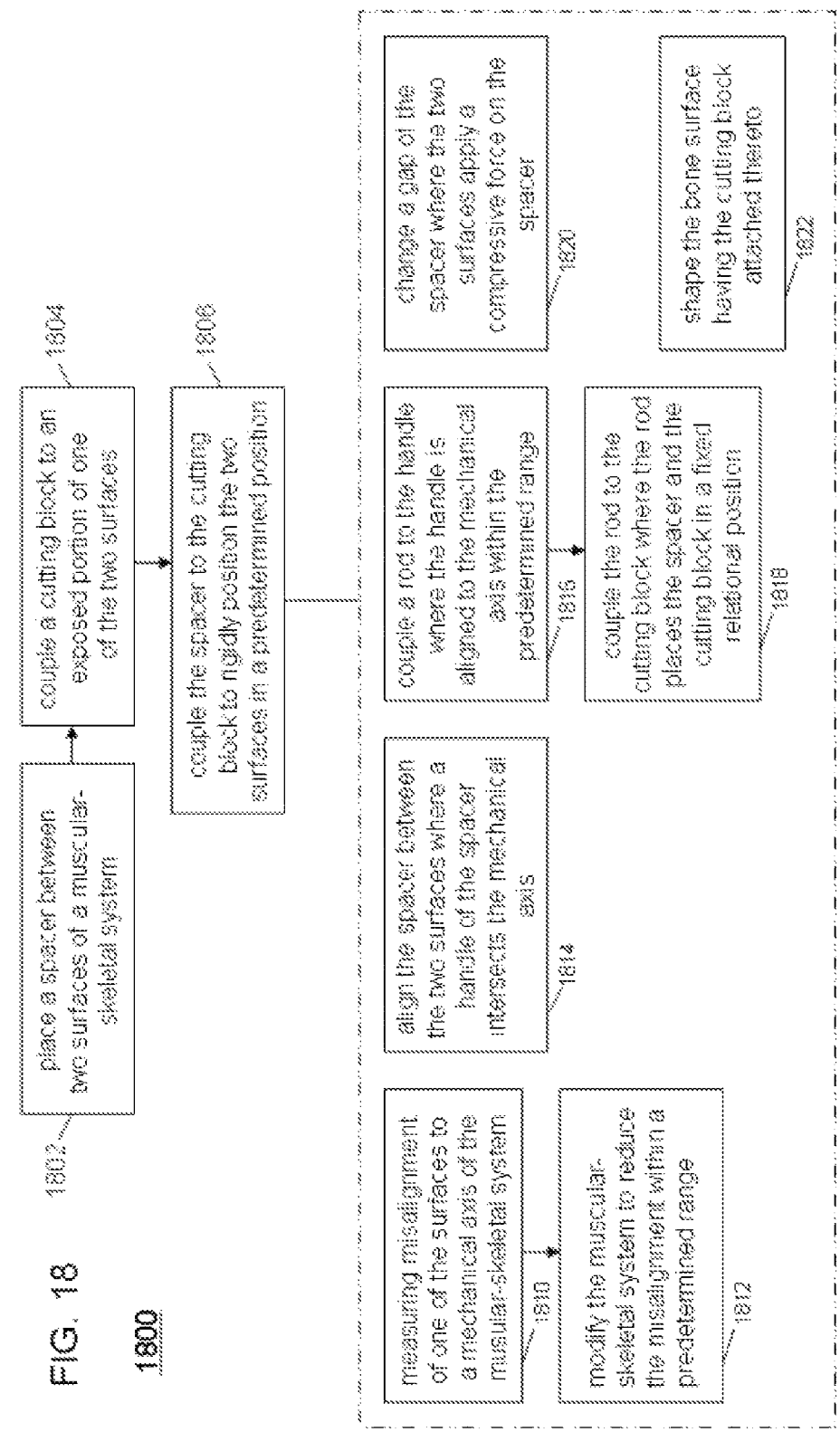
FIG. 18 is an exemplary method to place the muscular-skeletal system in a fixed position for bone shaping in accordance with an exemplary embodiment.

FIG. 18 is an exemplary method 1800 to place the muscular-skeletal system in a fixed position for bone shaping in accordance with an exemplary embodiment. The method can be practiced with more or less than the number of steps shown and is not limited to the order shown. A spacer is a device that as it names implies spaces two surfaces apart from each other. A spacer can have a fixed height or can be variable. In one embodiment, a spacer has an inferior surface and a superior surface for coupling to surfaces of the muscular-skeletal system. A spacer with a fixed height is also known as a spacer block in the orthopedic field. A spacer having variable height is known as a distractor.

In a step 1802, a spacer is placed between two surfaces of the muscular-skeletal system. The spacer separates the two surfaces of the muscular-skeletal system. In one embodiment, the spacer is placed between two bones. The superior surface of the spacer couples to a surface of a first bone and the inferior surface couples to a surface of a second bone. There can be other material or components between the superior and inferior surface of spacer and the bone surfaces. Thus, the spacer separates the first and second bone surfaces by at least the height of the spacer.

In a step 1804, a cutting block is coupled to an exposed portion of one of the two bone surfaces. A cutting block is a template for shaping a bone surface. It is typically fastened to a bone surface and can have slots and openings for guiding surgical tools such as a bone saw. In one embodiment, a cutting block is used to shape a bone end for receiving one or more artificial implant components or material. In many cases, the position of the cutting block is not arbitrary but has to have precision alignment. For example, when performing a joint replacement, the cutting block has to be positioned having one or more alignments to the muscular-skeletal system. Misalignment can cause joint failure and premature wear. An illustration of alignment will be disclosed in more detail by example hereinbelow.

In a step 1806, the spacer is coupled to the cutting block to rigidly position the two surfaces in a predetermined position. Cutting blocks are typically designed to be used to shape the bones with the two surfaces and more specifically the bones having the surfaces in a specific position and alignment. In one embodiment, the spacer is fixed in position to at least one of the bone surfaces. The spacer can be under compressive force due to muscle, ligaments and tendons coupling the first and second bones together. Alternatively, the spacer can be temporarily attached to one of the surfaces. For example, a surgical screw or pin can be used to fix the spacer position. If the spacer is a distractor, the compressive force can be adjusted by increasing or decreasing the height between the superior and inferior surfaces. The spacer can allow the two bones to move in relation to one another in a natural range of motion without movement of the device to the bone surface. The spacer and the cutting block are couple together to prevent movement of the first bone, second bone, bone surfaces, and cutting block. Coupling the spacer to the cutting block stabilizes the cutting block and keeps the first and second bones in a fixed relation to one another while the bone surface is shaped.

In a step 1810, the misalignment of at least one of the surfaces is measured in relation to a mechanical axis of the muscular-skeletal system. In general, alignment of the muscular-skeletal system is critical to obtain optimal performance and longevity. In fact, many problems that end up requiring surgery are due to misalignment or deformity that causes premature wear or damage to the muscular-skeletal system that can directly or indirectly result in a disability or health problem. Implanted devices and artificial joints follow similar constraints from a geometric standpoint since many mimic the natural device. Thus, the surgeon needs affirmation that the alignment of the muscular-skeletal system while modifying bone and soft tissue to receive implanted components. Typically, at least one of the bone surfaces has a relationship with a mechanical axis of the muscular-skeletal system. The mechanical axis is an optimal alignment of the bone or bone surface to another portion of muscular-skeletal system. In a non-limiting example, the bone surfaces and the thus the bones having the bone surfaces have an optimal alignment. This optimal alignment is known as the mechanical axis.

In one embodiment, a surface or feature of the handle corresponds to a surface of the muscular-skeletal system. This relationship can be used to compare the orientation of the surface or feature to a mechanical axis. The superior or inferior surface of the spacer couples to the surface (or reference surface). The surface of the spacer is shaped similarly to the reference surface. For example, if the reference surface of the muscular-skeletal system is planar, the spacer surface is also made planar and has a relational position of being co-planar or parallel to the reference surface. A feature or the surface of a feature such as an opening, recess, mounting structure can have a specific orientation to the reference surface. For example, an opening can have an orientation that is perpendicular to the reference surface. Thus, the opening will extend in a direction approximately perpendicular to the muscular-skeletal reference surface on which the spacer is coupled. The handle can have one or more surfaces or features made to have specific relational positions to one or both of the spacer surfaces. For example, at least one surface of the handle can be made co-planar to the spacer surface corresponding to the muscular-skeletal reference surface. The surface on the handle can be used to create features that have specific positional relationships to the plane of the muscular-skeletal reference surface to aid in determining misalignment. Measurement of misalignment will be discussed in more detail hereinbelow.

As disclosed hereinabove, the mechanical axis can be defined by placing targets overlying the patient that align to the axis or to reference points of the body. For illustrative purposes, the leg in extension will be used to describe a mechanical axis of the muscular-skeletal system for a knee joint replacement. The mechanical axis of the leg in extension is a straight line from the center of the femoral head, to the center of the knee joint, and continuing to the center of the ankle. The targets are placed above the mechanical axis and typically near the ankle region and the center of the femoral head. In one embodiment, the handle is aligned with the center of the knee joint and extends vertically from the knee. In a non-limiting example, a feature such as a center of at least one opening or a recess in the handle is geometrically aligned to the knee center and corresponds to a point on the mechanical axis. The mechanical axis corresponds to a straight line from a point on the ankle target (e.g. ankle center), to a point on the handle, and extending to a point on hip target (e.g. center of femoral head). Extending a plane of the mechanical axis vertically (e.g. 90 degrees to the horizontal plane) with the leg in extension would intersect the center of the feature on the handle. In the example, the proximal end of the tibia is prepared by the surgeon as a flat surface. Ideally, the mechanical axis of the intersects the plane of the prepared tibial surface at a right angle. In a non-limiting example, lasers are coupled openings or recesses in the handle of the spacer. The lasers point towards the ankle target and the hip target. The lasers are pointed at a 90-degree angle from the plane of the prepared bone surface. Thus, misalignment can be measured from the targets as the difference angle between the point where beams hit the target and the identified point on each target corresponding to the mechanical axis.

In a step 1812 the muscular-skeletal system is modified to reduce the misalignment within a predetermined range. Once the misalignment is measured the surgeon can determine if modification to the muscular-skeletal system is required and what type of modification is suitable to reduce the error. In general, keeping the misalignment within a predetermined range will improve consistency of the surgery. Implant manufacturers can use the surgical data to determine the sensitivity of misalignment to rework, patient problems, and implant longevity.

In a step 1814 the spacer is aligned between the two surfaces where a handle of the spacer intersects the mechanical axis. Typically, the spacer alignment occurs before the misalignment to the mechanical axis is measured. As disclosed above, the spacer is part of an alignment system. The spacer has a predetermined position or alignment between the first and second bone surfaces and more specifically on the reference bone surface. In one embodiment, the handle extends from the spacer and intersects the mechanical axis. In the non-limiting example, the spacer is placed on the prepared tibial surface such that a superior surface of the spacer mates with the condyles of the femur. Moreover, the handle extends centrally from the spacer with the leg in extension corresponding to the center of the knee joint (e.g. a point on the mechanical axis).

In a step 1816, a rod is coupled to the handle. The handle has a known relational positioning to the mechanical axis within the predetermined range as described hereinabove. In one embodiment, the rod fits into an opening in the handle. The rod can be fastened to the handle. For example, portions of the rod and the opening in the rod can be threaded. Alternatively, the rod can be held in place by a powerful magnet, clamp, screw, or other means. In general, the rod is rigid and projects the positional relationship of the handle (e.g. the bone reference surface). In the knee example, the tibia and femur are placed in flexion. More specifically, the tibia and femur are positioned having a 90-degree angle between the bones. The cutting block is on the exposed portion of the distal end of the femur to be shaped. Thus, the entire distal end of the femur is not shaped in this position.

In a step 1818, the rod is coupled to the cutting block. The rod is then coupled to both the handle and the cutting block. In one embodiment, the cutting block has a channel approximately the same diameter as the rod. The rod is placed in the channel of the cutting block. The rod fixes the position of the spacer and the cutting block. As mentioned previously, the spacer and the handle is within a predetermine range of the mechanical axis. In a non-limiting example, the rod extends along the mechanical axis. Placing the rod into the channel aligns the cutting block to the mechanical axis. The rod fixes the relational position of the first bone surface to the second bone surface. In the embodiment, the femur and tibia are aligned to the mechanical axis and positioned perpendicular to each other.

In a step 1820, the gap of the spacer is changed. In one embodiment, the spacer is a dynamic distractor. The dynamic distractor includes sensors to measure loading. As the gap of the distractor is increased the first and second bone surfaces apply a compressive force on the spacer. The muscle, ligaments, and tendons couple the two bones holding them together under tension. The gap can be adjusted to be within a predetermined measured loading range (at the distracted gap height).

In a step 1822, the bone surface is shaped. The cutting block is used as a template to direct a saw blade to shape the bone. With the rod rigidly holding the bone surfaces in place the cutting block is stabilized and in alignment with the mechanical axis. In the knee example, the exposed portion distal end of the femur can be shaped with the leg in flexion. The shaped surface can receive an implant that will be aligned correctly to the mechanical axis as well as the femur and tibia surfaces.

FIG. 19 is an exemplary method 1900 of measuring the muscular-skeletal system in accordance with an exemplary embodiment. The method can be practiced with more or less than the number of steps shown and is not limited to the order shown. In a non-limiting example a spacer is a device that separates two surfaces of the muscular-skeletal system. The spacer has an inferior surface and a superior surface that contact the two surfaces. The spacer can have a fixed height or can have a variable height. A fixed height spacer is commonly called a spacer block. The variable height spacer is known as a distractor. The use of spacer disclosed herein includes the spacer block and the distractor. In one embodiment, a handle extends from the spacer and typically resides outside or beyond the two surface regions being distracted. The handle is used to direct the spacer between the two surfaces. In one embodiment, the handle operatively couples to a lift mechanism of the distractor to increase and decrease a gap between the superior and inferior surfaces of the spacer. The spacer and handle is part of a system to measure alignment of the muscular-skeletal system. In one embodiment, at least one of the surfaces of the muscular-skeletal system that contacts the spacer has an optimal alignment to a mechanical axis of the muscular-skeletal system. The system measures the surface to mechanical axis alignment. In a non-limiting example, the surface can be corrected by a surgeon when the surface is misaligned to the mechanical axis outside a predetermined range.

A surface or feature of the handle has a relational position to the (reference or alignment) surface of the two surfaces that the spacer contacts. In one embodiment, the reference surface of the muscular-skeletal system is a planar surface. The surface of the spacer contacting the reference surface of is also planar and thus has the relational position of being planar or co-planar when coupled thereto. Similarly, the handle is attached or coupled to the spacer block or distractor having a relational position to the surface of the spacer that contacts the reference surface. Typically, the relational position of the surface or feature on the handle is co-planar or perpendicular to the surface of the spacer.

The two surfaces of the muscular-skeletal system are typically positioned in predetermined relation before measuring misalignment to the mechanical axis. The predetermined relation typically corresponds to a natural position of the muscular-skeletal system. For example, a common position is the tibia positioned 180 degrees from the femur, which is commonly known as a leg in extension. In this example, the reference surface is a proximal tibial surface of the tibia. In one embodiment, the proximal tibial surface is a planar surface prepared by the surgeon. Ideally, the tibial surface is formed perpendicular to the mechanical axis with the leg in extension. A measurement of the tibial surface to the mechanical axis is performed to verify that it is within a predetermined range or specification. Similarly, a measurement is often taken with the muscular-skeletal system in a second predetermined relation. The second predetermined relation is typically at a different point in the range of natural motion. For example, the leg in extension with the tibia positioned 90 degrees from the femur. One or more sensors such as accelerometers can be use to measure the relational positioning of the two surfaces of the muscular-skeletal system.

In one embodiment, a feature such as an opening or cavity is formed in the handle. The opening or cavity has a relational positioning to the reference surface when the spacer block or distractor is placed between the two surfaces of the muscular-skeletal system. In a non-limiting example to illustrate the relational positioning, the opening or cavity is perpendicular to the plane of the reference surface. In the example where the mechanical axis is ideally perpendicular to the reference surface a rod is placed in the opening or cavity. The rod is directed perpendicular to the plane of the reference surface. A comparison of the direction of the rod to the mechanical axis yields misalignment of the reference surface to the ideal. The surgeon can use the rod with landmarks that identify the mechanical axis to make a visual determination of alignment. Alternatively, the rod can be used to measure an angle difference between the mechanical axis and the actual muscular-skeletal alignment. Furthermore, the rod can include one or more sensors for measuring a parameter of the muscular-skeletal system including alignment.

In another embodiment, targets are placed on the muscular-skeletal system aligned with the mechanical axis. An axis point or axis line on the target aligns with the mechanical axis. A laser is placed in the opening or cavity on the handle. In a non-limiting example, the center of the opening or cavity corresponds to an axis point on the mechanical axis. The mechanical axis is a straight line between the center of the opening and one or more targets. The beam of the laser is directed to the target. Using the example above, the beam is directed perpendicular to the plane of the reference surface to the target. The position where the beam hits the target corresponds to misalignment of the reference surface to the mechanical axis. The misalignment results in the beam hitting the target on either side of the axis point or line. In a similar fashion the location of the beam on the target could also be used to determine if the reference surface has a slope by viewing where the beam hits the target in an opposite plane. For example, if the misalignment measurement is on a horizontal plane relative to the axis point, a slope of the reference surface can correspond to the beam location on a vertical plane or above/below the axis point.

In a step 1902, two surfaces of the muscular-skeletal system are distracted with a spacer. The gap between the two surfaces can be varied with the distractor. In a step 1904, an alignment aid is coupled to a handle of the distractor. The misalignment of a surface (e.g. reference surface) of the two surfaces to a mechanical axis is measured with an alignment aid that is coupled to a handle of the distractor. The alignment aid is coupled to a surface or feature of the handle of the distractor that has a relational position to the reference surface. In one embodiment, an alignment aid can be a laser and at least one target. Referring to a step 1926, at least one laser is coupled to the handle of the distractor. In one embodiment, the at least one laser is coupled to a feature such as an opening or cavity. In a step 1928, at least one target is coupled to the muscular-skeletal system. In general, the at least one target can be placed overlying the muscular-skeletal system such in a location corresponding to an axis point of the mechanical axis. An axis point on the target aligns to the mechanical axis. The beam from the laser hits the target. The point where the beam hits is compared to the axis point of the target that corresponds to the mechanical axis. The target can have a scale that measures misalignment of the surface to the mechanical axis. As disclosed above, the direction of the laser corresponds to the surface of the muscular-skeletal system.

In a step 1906, the two surfaces of the muscular-skeletal system are placed in a first position. The misalignment of the surface to the mechanical axis is measured. In a step 1908, the misalignment is corrected if the measurement is outside a predetermined range. In general, data generated by this system can yield significant information on how misalignment affects the muscular-skeletal system. The data can be used to further identify the optimal predetermined range that minimizes the effect of misalignment and consistently produces a positive outcome. In a step 1910, the gap or the space between the inferior and superior surfaces of the spacer is measured. In a step 1912, a force, pressure, or load applied by the two surfaces of the muscular-skeletal system on the distractor is measured. One or more sensors can be placed in the superior or inferior surfaces to measure a parameter such as but not limited to force, pressure, or load. The two surfaces of the muscular-skeletal system apply pressure or force to the superior and inferior surfaces of the spacer and more specifically on at least one sensor on either surface of the distractor. The measurements of steps 1908, 1910, and 1912 are completed with the muscular-skeletal system in the first position. As mentioned above, the first position is typically a geometrically significant position of the muscular-skeletal system that allows comparison to the mechanical axis. The measurement data is transmitted to a processing unit for viewing on a display and for long-term storage. The system allows for real time measurement if and when the muscular-skeletal system is modified with the distractor in place.

The following measurements steps are similar to the measurements in the first position described above. In a step 1916, the two surfaces of the muscular-skeletal system are placed in a second position. The misalignment of the surface to the mechanical axis can be measured in the second position to verify alignment. In a step 1918, the misalignment is corrected in if the measurement is outside a predetermined range. In a step 1920, the gap or the space between the inferior and superior surfaces of the spacer is measured. In a step 1922, a force, pressure, or load applied by the two surfaces of the muscular-skeletal system on the distractor is measured. The measurements of steps 1918, 1920, and 1922 are completed with the muscular-skeletal system in the second position. As mentioned above, the second position is also a geometrically significant position of the muscular-skeletal system that allows comparison to the mechanical axis. The measurement data is transmitted to the processing unit. The system allows for real time measurement in the second position.

FIG. 20 is an exemplary method 2000 of a disposable orthopedic system in accordance with an exemplary embodiment. The method can be practiced with more or less than the number of steps shown and is not limited to the order shown. In a step 2002, at least one parameter of the muscular-skeletal system is measured with a sensor. As disclosed hereinabove, the sensor provides accurate measurements of parameters such as distance, weight, strain, load, pressure, force wear, vibration, viscosity, and density. In one embodiment, the sensor is a disposable sensor. In a non-limiting example, the disposable sensor is adapted to an orthopedic device such as a tool or implantable component. The sensor is sterilized and placed in a package that maintains sterility. The sensor is typically contaminated with biological material when used to measure the muscular-skeletal system during a surgical procedure. In a step 2004, the sensor is disposed of after use. The sensor is disposed of as biological waste if contaminated by biological material during the procedure. Packaging of a single use device greatly reduces cost, as the housing does not have to withstand repeated cleanings. Moreover, it eliminates the cost of a sterilization process. In a non-limiting example, the sensor is used in orthopedic surgery and more specifically to provide intra-operative measurement during joint implant surgery.

In a step 2022, the sensor is powered. In one embodiment, the sensor is not powered until it is used. The sensor can have a temporary power source that powers the device for a procedure. A charger can be provided to charge the unit up prior to use. The power source can be internal to the sensor to prevent issues with sterility. The temporary power source can sustain the device for a predetermined period of time that is sufficient for the procedure but prevents reuse of the device. The sensor is in communication with a processing unit. In one embodiment, the processing unit is located external to the sensor. In the surgical example, the processing unit is located outside of the immediate surgical area. For illustration purposes, the processing unit is a microprocessor of a notebook computer.

In a step 2024, patient information is inputted to the processing unit. The patient information can input through a variety of methods. For example, the information can be typed in, scanned in, downloaded via radio frequency tag, or verbally transmitted, recorded, and converted. The patient information can be displayed on a screen of the notebook computer. The patient information can include personal, medical, and specific information related to the procedure.

In a step 2026, a reader is coupled to the processing unit. The reader can be wired or wireless. In a step 2028, the reader is used to scan in information pertaining to the procedure. In one embodiment, the reader is used to scan in components of the system such as the sensors, alignment aids, implant components, and other devices prior to use. In a non-limiting example, the information can be used for identification of the specific components (e.g. serial numbers) used during the procedure. The information can be used for billing, patient records, long term monitoring of components, and component recall.

In a step 2006, the sensor is placed between two surfaces of the muscular-skeletal system. The sensor measures a parameter in proximity to the surfaces of the muscular-skeletal system. In one embodiment, the two surfaces are exposed by incision. For example, the sensor has a small form factor allowing it to be placed in or on a spacer. A spacer separates the two surfaces of muscular-skeletal system. Examples of a spacer are a spacer block or a distractor. In a non-limiting example, a joint of the muscular-skeletal system is exposed. One or more of the joint surfaces can be shaped or prepared by the surgeon. The spacer block or distractor is placed between the joint surfaces of the muscular-skeletal system. The sensor can have an exposed surface that will contact at least one of the two surfaces.

In a step 2008, a load, force, or pressure applied by the two surfaces on the sensor is measured. For example, the spacer block or distractor distracts the joint of the muscular-skeletal system. A measurement of the load, force, or pressure is measured by the sensor for a spacing or gap. The gap is the distance between the two surfaces of the muscular-skeletal system. In a step 2016, a gap can be varied between the two surfaces of the muscular-skeletal system with the spacer in place. In one embodiment, the gap is varied by a distractor between the two surfaces. The distractor includes a lift mechanism that can increase or decrease a gap between the two surfaces. The sensor can measure one or more parameters at each gap height.

In a step 2010, the sensor is placed in a cavity of a surface of a spacer. In general, a spacer has a superior and inferior surface. The superior and inferior surfaces are placed between the two surfaces of the muscular-skeletal system. The superior and inferior surfaces come in contact with the two surfaces of the muscular-skeletal system under distraction. In one embodiment, one of the inferior or superior surfaces of the spacer have a cavity or recess for receiving the sensor. The sensor is placed in the cavity exposing a surface of the sensor. The surface of the sensor can be planar with the surface of the spacer. As disclosed above, the spacer can be placed between the two surfaces of the muscular-skeletal system such that the surface of the sensor is in proximity or in contact with one or both of the surfaces.

In a step 2012, the sensor is removed from the cavity or recess. The sensor can have a feature that simplifies removal from the superior or inferior surface of a device. For example, the sensor can have a tab, indentation, or surface feature that allows removal by hand or with a tool. Alternatively, the device in which the sensor is placed can have a mechanism to push the sensor out of the recess. In a step 2014, the sensor is disposed of after being removed from the cavity or recess.

In a step 2018, an alignment of a surface to a mechanical axis is measured with an alignment aid. In general, at least one of the two surfaces of the muscular-skeletal system has an alignment with a mechanical axis of the muscular-skeletal system. The alignment to the mechanical axis needs to be preserved or corrected during the procedure. Similar to the sensor above, components of the alignment aid are designed for a single use. In one embodiment, the mechanical axis is identified. Similarly, the surface of the muscular-skeletal system is compared to the mechanical axis. The difference between the mechanical axis and surface of the muscular-skeletal system is a measure of the misalignment. Adjustments to the muscular-skeletal system can be performed to reduce misalignment within a predetermined range. In a step 2020, at least one component of the alignment aid is disposed of after the procedure is completed.

FIG. 21 is an exemplary method 2100 of a disposable orthopedic system in accordance with an exemplary embodiment. The method can be practiced with more or less than the number of steps shown and is not limited to the order shown. In a step 2102, an alignment of a surface to a mechanical axis is measured with an alignment aid. In general, a mechanical axis is identified by the alignment aid. The mechanical axis is then compared to an alignment of one or more surfaces or structures of the muscular-skeletal system. Ideally, the difference or misalignment of the surfaces or structures to the mechanical axis should be within a predetermined range that places the surfaces or structures in an optimal muscular-skeletal kinematic setting.

In a non-limiting example, targets and more specifically a point on each target correspond to points on the mechanical axis. The targets are coupled to the muscular-skeletal system in proximity to the surfaces of the muscular-skeletal system. The surfaces can be part of structures of the muscular-skeletal system such as bones, muscles, ligament, tendons, and cartilage. The structures corresponding to the surfaces can have a relational positioning in 3D space that relate to the position of the surfaces to each other. In one embodiment, the surface is between the targets. Alternatively, the targets can be placed having an unobstructed path to the surface that allows measurement. The targets can also align having a more complex geometry to represent the mechanical axis. One or more lasers are mounted at a height where a beam from a laser will hit the target unless grossly misaligned. The laser is mounted having a predetermined positional relationship to the plane of the surface. For example, the laser is directed 90 from the plane of the surface corresponding to a direction of the mechanical axis. The targets can have calibration markings to indicate a measure of misalignment. The beam from the laser will hit the point on each target if the plane of the surface is aligned correctly to the mechanical axis. Conversely, the distance from the point on each target is representative of the misalignment. The calibration marking where the beam hits represents the misalignment. Adjustments to the muscular-skeletal system can be performed to reduce misalignment within a predetermined range. In a step 2104, at least one component of the alignment aid is disposed of after the procedure is completed. For example, the targets or lasers that are within the surgical field.

In one embodiment, the alignment is performed with a distractor between the two surfaces of the muscular-skeletal system. The distractor separates the surfaces of the muscular-skeletal system. In a step 2122, the two surfaces of the muscular-skeletal system are distracted when measuring alignment. The distractor can vary the gap between the two surfaces of the muscular-skeletal system allowing measurements to be taken with varying gap heights.

In a step 2106, at least one parameter of the muscular-skeletal system is measured with a sensor. As disclosed hereinabove, the sensor provides accurate measurements of parameters such as distance, weight, strain, load, pressure, force wear, vibration, viscosity, and density. In one embodiment, the sensor is a disposable sensor. In a step 2108, the sensor is disposed of after use. The sensor is disposed of as biological waste if contaminated by biological material during the procedure. A disposable sensor provides data for providing quantitative data on the procedure without the large capital expenditure required for traditional measuring equipment.

In general, data is collected relevant to the procedure. For example, patient information and component information can be collected and stored in an electronic format prior to the procedure being performed. Component information can relate to products used in the procedure such as serial number, date of production, model number, and other related data that identifies the product. In a step 2014, the sensor is powered. In one embodiment, the sensor is not powered until it is used. Once enabled, the sensor can establish communication with a processing unit. The processing unit can be a collection point for information. The processing unit is coupled to memory that can store information locally or send the information to a database. Similarly, the sensor can have information pertaining to the sensor product stored in memory. The sensor can send this information to the processing unit as part of the information collection process. In a step 2116, patient information is input and provided to the processing unit. The patient information can be input through a variety of methods. For example, the information can be typed in, scanned in, downloaded via radio frequency tag, or verbally transmitted, recorded, and converted. The patient and component information can be displayed on a screen coupled to the processing unit for use by the surgeon or other healthcare providers. The patient information can be encrypted to prevent access by unauthorized people. The patient information can include personal, medical, and specific information related to the procedure. In a step 2118, a reader is coupled to the processing unit. The reader can be wired or wireless. In a step 2120, the reader is used to scan in information pertaining to the procedure. In one embodiment, the reader is an alternate approach of data collection of components and information. The reader is used to scan and input information displayed on components or packaging of components. The information can be used for billing, patient records, long term monitoring of components, and component recall.

In a step 2110, data measured by the sensor is transmitted to the processing unit. The system dynamically measures a parameter of the muscular skeletal system. For example, the system can measure the parameter when the muscular-skeletal system is placed in different positions whereby the position of the surfaces also differs. Another example is modification of the muscular-skeletal system. The sensor reading adjusts as the modification of the muscular-skeletal system changes the parameter being measured. In a step 2112, the data is displayed in real time on the display. In one embodiment, the sensor transmits data as soon as a measurement is taken. The data is then processed by the processing unit and displayed in a format that aids the surgeon or healthcare worker. Thus, any change in the parameter is stored and displayed while the sensor is enabled.

In summary, the invention describes a system to define the joint gap, bone preparation, alignment, load, and balance by measurement. Furthermore the surgeon obtains the information in real time from the system while soft tissue release and alignment is being performed. The graphic user interface can be in the device itself or integrated with a processing unit and display in the operating room. The sensors can be incorporated into tools and equipment for measuring the muscular-skeletal system pre-operatively, intra-operatively, post-operatively, and long term. The sensors or sensor system is in communication with a data registry and repository to generate statistically significant data that can be used as clinical evidence. The data repository and registry further includes information used in evidentiary based orthopedic medicine. This invention while intended for use in the medical field and more specifically orthopedics uses a knee application to illustrate principles of the system and method for illustrative purposes only and can be similarly adapted for the hip, shoulder, ankle, spine, as well as to measure other parameters of a biological system.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An orthopedic system comprising:
   a spacer having a superior surface and an inferior surface for coupling between at least two bones of a muscular-skeletal system;
   a handle coupled to the spacer;
   a cutting block; and
   a rod directly connected to the handle, where the rod is coupled to the cutting block to stabilize and align the cutting block; where the handle has a predetermined alignment to a surface of one of the at least two bones of the muscular-skeletal system and where the surface is aligned to a mechanical axis of the muscular-skeletal system; further including an alignment tool coupled to the handle to measure misalignment of the surface to the mechanical axis; where the alignment tool comprises at least one laser coupled to the handle; and at least one target coupled to the muscular-skeletal system where the target is positioned to be in alignment with the mechanical axis and where a beam of the laser hits the target to measure the misalignment of the surface to the mechanical axis.

2. The system of claim 1 where the alignment tool is a rod coupled to the handle.

3. The system of claim 1 further including at least one sensor in a recess on either the superior or inferior surface of the spacer, where a portion of the at least one sensor forms a portion of the superior surface or a portion of the inferior surface, to measure at least one parameter of the muscular-skeletal system.

4. The system of claim 1 where the handle intersects the mechanical axis.

5. The system of claim 1 where a gap between the superior surface and the inferior surface is adjustable.

6. The system of claim 1 where the at least two bones apply a compressive force on the spacer and where the spacer, rod, and cutting block rigidly position the at least two bones in alignment to the mechanical axis.

7. A distraction system comprising:
   a distractor comprising:
      a first support structure having a superior surface;
      a second support structure having an inferior surface; and
      a lift mechanism coupled to interior surfaces of the first and second support structures;
   a handle operatively coupled to the lift mechanism;
   a cutting block; and
   a rod directly connected to the handle, where the rod is coupled to the cutting block to stabilize and align the cutting block to the distractor; further including an alignment tool coupled to the handle of the distractor where at least one surface of the handle has a predetermined alignment with either the superior or inferior surface of the support structure; further including a rod coupled to the handle where the handle aids in determining misalignment to a mechanical axis of the muscular-skeletal system; further including at least one laser coupled to the handle; and at least one target coupled to the muscular-skeletal system where the target is positioned to be in alignment with a mechanical axis of the muscular-skeletal system and where a beam of the laser hits the target to measure the misalignment of the surface to the mechanical axis.

8. The system of claim 7 further including:
   at least one sensor coupled to either the first or second support structure for measuring a parameter of a muscular-skeletal system, where a portion of the at least one sensor forms a portion of the superior surface or a portion of the inferior surface; and
   a processing unit external to the at least one sensor where the processing unit is in communication with the at least one sensor for receiving measured parameter data.

* * * * *